(12) United States Patent
Thomas et al.

(10) Patent No.: US 10,255,723 B2
(45) Date of Patent: *Apr. 9, 2019

(54) PLANNING, NAVIGATION AND SIMULATION SYSTEMS AND METHODS FOR MINIMALLY INVASIVE THERAPY

(71) Applicant: SYNAPTIVE MEDICAL (BARBADOS) INC., Bridgetown (BB)

(72) Inventors: Monroe M. Thomas, Toronto (CA); Gal Sela, Toronto (CA); Cameron Piron, Toronto (CA); Joshua Richmond, Toronto (CA); Murugathas Yuwaraj, Markham (CA); Wes Hodges, London (CA); Simon Alexander, Toronto (CA); David Gallop, Toronto (CA); William Lau, Toronto (CA); Sheryl Thingvold, Toronto (CA); Kelly Dyer, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,946

(22) Filed: Jul. 11, 2017

(65) Prior Publication Data
US 2017/0309069 A1 Oct. 26, 2017

Related U.S. Application Data

(63) Continuation of application No. 15/422,683, filed on Feb. 2, 2017, now Pat. No. 9,734,632, which is a
(Continued)

(51) Int. Cl.
*G06K 9/00* (2006.01)
*G06T 19/00* (2011.01)
(Continued)

(52) U.S. Cl.
CPC .......... *G06T 19/003* (2013.01); *A61B 5/0042* (2013.01); *A61B 5/055* (2013.01);
(Continued)

(58) Field of Classification Search
CPC ............... A61B 6/00; G06K 9/00; G06T 7/00
(Continued)

(56) References Cited

U.S. PATENT DOCUMENTS 6,112,750 A * 9/2000 Chandra ............. G06F 19/3481
128/898
6,505,065 B1 1/2003 Yanof et al.
(Continued)

FOREIGN PATENT DOCUMENTS

CN 102448398 A 5/2012
CN 102264312 B 9/2016
(Continued)

OTHER PUBLICATIONS

Office Action dated May 28, 2018 issued in relation to corresponding Chinese patent application No. 2014800153202 (2 pages).
(Continued)

*Primary Examiner* — Abolfazl Tabatabai

(57) ABSTRACT

Disclosed herein are planning, navigation and simulation systems and methods for minimally invasive therapy in which the planning method and system uses patient specific pre-operative images. The planning system allows for multiple paths to be developed from the pre-operative images, and scores the paths depending on desired surgical outcome of the surgery and the navigation systems allow for minimally invasive port based surgical procedures, as well as craniotomies in the particular case of brain surgery.

20 Claims, 10 Drawing Sheets

Related U.S. Application Data continuation of application No. 14/769,668, filed as application No. PCT/CA2014/050272 on Mar. 14, 2014, now Pat. No. 9,600,138.

(60) Provisional application No. 61/924,993, filed on Jan. 8, 2014, provisional application No. 61/800,155, filed on Mar. 15, 2013, provisional application No. 61/845,256, filed on Jul. 11, 2013, provisional application No. 61/900,122, filed on Nov. 5, 2013.

(51) Int. Cl.

| | | |
|---|---|---|
| *G06T 19/20* | (2011.01) | |
| *G06T 11/20* | (2006.01) | |
| *A61B 34/20* | (2016.01) | |
| *A61B 6/03* | (2006.01) | |
| *A61B 5/00* | (2006.01) | |
| *A61B 6/00* | (2006.01) | |
| *A61B 8/08* | (2006.01) | |
| *G06F 3/0481* | (2013.01) | |
| *G06T 1/60* | (2006.01) | |
| *G06T 17/00* | (2006.01) | |
| *G06T 7/00* | (2017.01) | |
| *G06F 3/0484* | (2013.01) | |
| *A61B 5/055* | (2006.01) | |
| *A61B 5/05* | (2006.01) | |
| *A61B 90/00* | (2016.01) | |
| *A61B 34/10* | (2016.01) | |
| *A61B 8/00* | (2006.01) | |

(52) U.S. Cl.
CPC .............. *A61B 6/032* (2013.01); *A61B 6/037* (2013.01); *A61B 6/501* (2013.01); *A61B 8/0808* (2013.01); *A61B 34/10* (2016.02); *A61B 34/20* (2016.02); *G06F 3/04815* (2013.01); *G06F 3/04842* (2013.01); *G06F 3/04847* (2013.01); *G06T 1/60* (2013.01); *G06T 7/0012* (2013.01); *G06T 11/20* (2013.01); *G06T 17/00* (2013.01); *G06T 19/20* (2013.01); *A61B 8/00* (2013.01); *A61B 2034/105* (2016.02); *A61B 2034/107* (2016.02); *A61B 2034/2051* (2016.02); *A61B 2034/2055* (2016.02); *A61B 2090/378* (2016.02); *A61B 2090/3735* (2016.02); *G06T 2200/04* (2013.01); *G06T 2200/24* (2013.01); *G06T 2207/10088* (2013.01); *G06T 2207/20101* (2013.01); *G06T 2207/30016* (2013.01); *G06T 2207/30241* (2013.01); *G06T 2210/41* (2013.01); *G06T 2219/028* (2013.01)

(58) Field of Classification Search
USPC .... 380/128–134; 600/1, 9, 23, 26, 407, 410, 600/411, 427, 439; 128/845
See application file for complete search history.

(56) References Cited

U.S. PATENT DOCUMENTS

| | | | |
|---|---|---|---|
| 9,734,632 B2* | 8/2017 | Thomas | ................ G06T 19/003 |
| 2007/0249911 A1 | 10/2007 | Simon | |
| 2009/0259230 A1 | 10/2009 | Khadem et al. | |
| 2012/0184844 A1 | 7/2012 | Gielen et al. | |
| 2012/0253515 A1 | 10/2012 | Coste-Maniere et al. | |

FOREIGN PATENT DOCUMENTS

| | | |
|---|---|---|
| JP | 2002017753 | 1/2002 |
| JP | 2010540021 | 12/2010 |
| JP | 2012533333 | 12/2012 |
| WO | 2011007318 | 1/2011 |
| WO | 2011128823 | 10/2011 |
| WO | 2012092511 A2 | 7/2012 |
| WO | 2012098485 A1 | 7/2012 |

OTHER PUBLICATIONS

Office Action dated Feb. 26, 2018 issued in relation to corresponding Japanese patent application No. 2015-561870 (6 pages).

* cited by examiner

PLANNING, NAVIGATION AND SIMULATION SYSTEMS AND METHODS FOR MINIMALLY INVASIVE THERAPY

CROSS-REFERENCE TO RELATED APPLICATIONS

This application is a Continuation of U.S. patent application Ser. No. 15/422,683, filed Feb. 2, 2017, which is a Continuation of National Phase patent application Ser. No. 14/769,668 claiming the benefit of the international PCT Patent Application No. PCT/CA2014/050272, filed on Mar. 14, 2014, in English, which claims priority to U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013, the entire contents of which are incorporated herein by reference.

This application also claims priority to U.S. Provisional Application No. 61/924,993, titled "PLANNING, NAVIGATION AND SIMULATION SYSTEMS AND METHODS FOR MINIMALLY INVASIVE THERAPY" and filed on Jan. 8, 2014, the entire contents of which is incorporated herein by reference.

This application also claims priority to U.S. Provisional Application No. 61/845,256, titled "SURGICAL TRAINING AND IMAGING BRAIN PHANTOM" and filed on Jul. 11, 2013, the entire contents of which is incorporated herein by reference.

This application also claims priority to U.S. Provisional Application No. 61/900,122, titled "SURGICAL TRAINING AND IMAGING BRAIN PHANTOM" and filed on Nov. 5, 2013, the entire contents of which is incorporated herein by reference.

FIELD

The present disclosure relates to planning, navigation and simulation systems and methods for minimally invasive therapy.

BACKGROUND

In the field of medicine, imaging and image guidance tends to be a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy.

Targeted stem cell delivery, adaptive chemotherapy regimens, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI tends to enable three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using different physical principals available with each modality.

CT is often used to visualize boney structures, and blood vessels when used in conjunction with an intra-venous agent such as an iodinated contrast agent. MRI may also be performed using a similar contrast agent, such as an intravenous gadolinium based contrast agent which has pharmaco-kinetic properties that enable visualization of tumors, and break-down of the blood brain barrier.

These multi-modality solutions may provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with associated contrast, such as iodinated contrast, as well as MRI scans with associated contrast, such as gadolinium contrast. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Previously known systems for multi-modality imaging for planning and navigation include integration of the imaging data of the surgery suite in an operating room. Technologies have allowed these three-dimensional modalities, including PET, CT, MRI, 3D US and two-dimensional modalities such as X-ray and US, to be viewed together to create image sets, used in the operating room. These image sets can be used to assist surgeons in better resecting diseased tissue such as cancer, to guide repair of vascular defects such as stroke and ICH, to deliver therapies for psychiatric conditions such as major depression or obsessive compulsive disorder, to perform procedures such as deep brain stimulation ("DBS") for Parkinson's, Alzheimer's and Huntington's, and to guide radiation oncologists for radiation therapy for brain tumors.

These solutions have attempted to integrate different imaging modalities into the surgical suite, by use of intraoperative imaging; for example by registering and tracking real-time US images; by use of "C" shaped arms for X-ray or CT imaging ("C-arms"); for instance, by use of dedicated MRI systems for specific parts of the anatomy, such as the head; as well as use of movable MRI systems. Generally, these systems do not take full advantage of the ability to achieve better imaging with the improved access afforded by the surgical procedure itself, nor is the information acquired integrated into the procedure in ways that address the fundamental challenges associated with the disease management.

There is therefore a need for a multi-modality imaging system and method that achieves surgical planning and navigation by analyzing input(s) retrieved through the improved tissue access resulting from the surgical procedures themselves.

Furthermore, there is a need for effective recording registration or integrating images and other inputs in a meaningful way. Additionally, there is a need to integrate other valuable data points related to surgical tools, or physics of the tissues themselves. There is therefore a need for a multi-modality imaging system and method that achieves surgical planning and navigation by meaningfully integrating a number of data points retrieved during, before and after surgery to provide improved surgical and navigation systems. There is also a need for a system and method that utilizes information specific to the surgical procedure and tools to provide improved navigation and planning.

Furthermore, imaging in current solutions is often performed on large sections of tissue, such as brain tissue, accessed by open surgical approaches that are highly invasive to the patient. There is also a growing class of procedures, including neurosurgical procedures, which ideally would require only minimally invasive navigation and imaging system approaches. For example, ICH repair, stroke repair, deep brain tumor surgery, intra-axial brain tumor surgery, endo-nasal surgery, such as pituitary or brain-stem surgery, stem-cell therapy, directed drug delivery, and deep brain stimulator delivery are all examples of procedures that are well suited to minimally invasive approaches. Many surgical approaches in neurosurgery have become more dependent on minimally invasive approaches to resect diseased tissue, modify vascular and clotting issues, and maintain as much healthy neural tissue as possible. Current intra-operative surgical systems such as navigation and imaging solutions, however, tend to be lacking. Although approaches to remove tissue through endo-nasal approaches, access port-based approaches, and positioning of electrical stimulation devices have become important procedures, medical imaging and navigation procedures have not evolved to accommodate the specific needs of these approaches.

There is therefore a need for a multi-modality imaging system and method that achieves surgical planning and navigation through minimally invasive means and approaches.

Also, as port based procedures are relatively new, the detailed application of imaging to such a procedure has not been anticipated, nor has the interface between known devices' impact on tissue been integrated into a planning system. In craniotomies, the complexity of the multiple contrast mechanisms used in known systems can overwhelm software system architectures. Furthermore, the complexities associated with tissue shift that occurs during surgery are not well addressed. There is therefore a need for a system and method for pre-operative and intra-operative planning and navigation to allow for minimally invasive port based surgical procedures, as well as larger, open craniotomies.

In current systems, a radiologist, neurologist, surgeon or other medical professional normally selects an imaging volume based on diagnostic imaging information, or clinical information related to the patient. This imaging volume is often associated with a suggested trajectory to approach the surgery, for instance a needle insertion path. One disadvantage of current systems, however, is that this information regarding tumor location and trajectory can typically not be modified or interacted with in the surgical suite, resulting in limited utility of this detailed information if additional information during the surgery comes to light, for instance the location of a vessel or critical structure in conflict with the pre-selected trajectory. There is therefore a need for a system that provides real-time surgical procedure planning correction.

SUMMARY

The present invention is directed to a planning system for minimally invasive therapy. In the present invention systems and methods are provided for planning a pathway to a target location in tissue within a patient's body. The system consists of a storage medium to store pre-operative imaging volumes, a surgical outcome criteria associated with anatomical portions of the body, and a processor, in communication with the storage medium and outcome criteria, to identify, score and save one or more surgical trajectory paths.

In one embodiment, the system comprises a storage device, a computer processor that works cooperatively to receive, store and compute inputs and surgical trajectory paths, and displays the results on a user interface.

In a further embodiment, a computer implemented method for planning a pathway location to a tissue within a patient's body is disclosed. The method comprises the steps of receiving inputs through the user interface of a computer, producing a 3D image containing entry points to the tissue, computing and storing one or more surgical trajectory paths based on a surgical outcome criteria, and displaying a selected trajectory path at the user interface.

A system for planning brain surgery is further disclosed. The system comprises a storage device to store at least one pre-operative 3D imaging volume, and a computer processor that receives inputs (i.e., sulci entry points, target locations, surgical outcome criteria, 3D imaging volume), computes a score based on a surgical outcome criteria and displays one or more trajectory paths based on the score.

In a further embodiment, a system for planning a pathway location to a tissue within a patient's body is disclosed. The system comprises a storage medium, a display, a user interface and a computer program with multiple code segments configured to produce a 3D image, receive user inputs, compute one or more point-wise trajectory paths related to a surgical outcome criteria, and assigning a relevant score to the one or more trajectory paths.

In a further embodiment, a system for planning a pathway location to a tissue within a patient's body is disclosed. The system comprises a storage medium, a display, a user interface and a computer program with multiple code segments configured to produce a 3D static or animated image, receive user inputs, store a pre-operative imaging volume, compute one or more point-wise trajectory paths relative to known points in the imaging volume that relate to a surgical outcome criteria, assigning a score to the one or more trajectory paths, and exporting the one or more such paths.

A further understanding of the functional and advantageous aspects of the invention can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Figure 1:
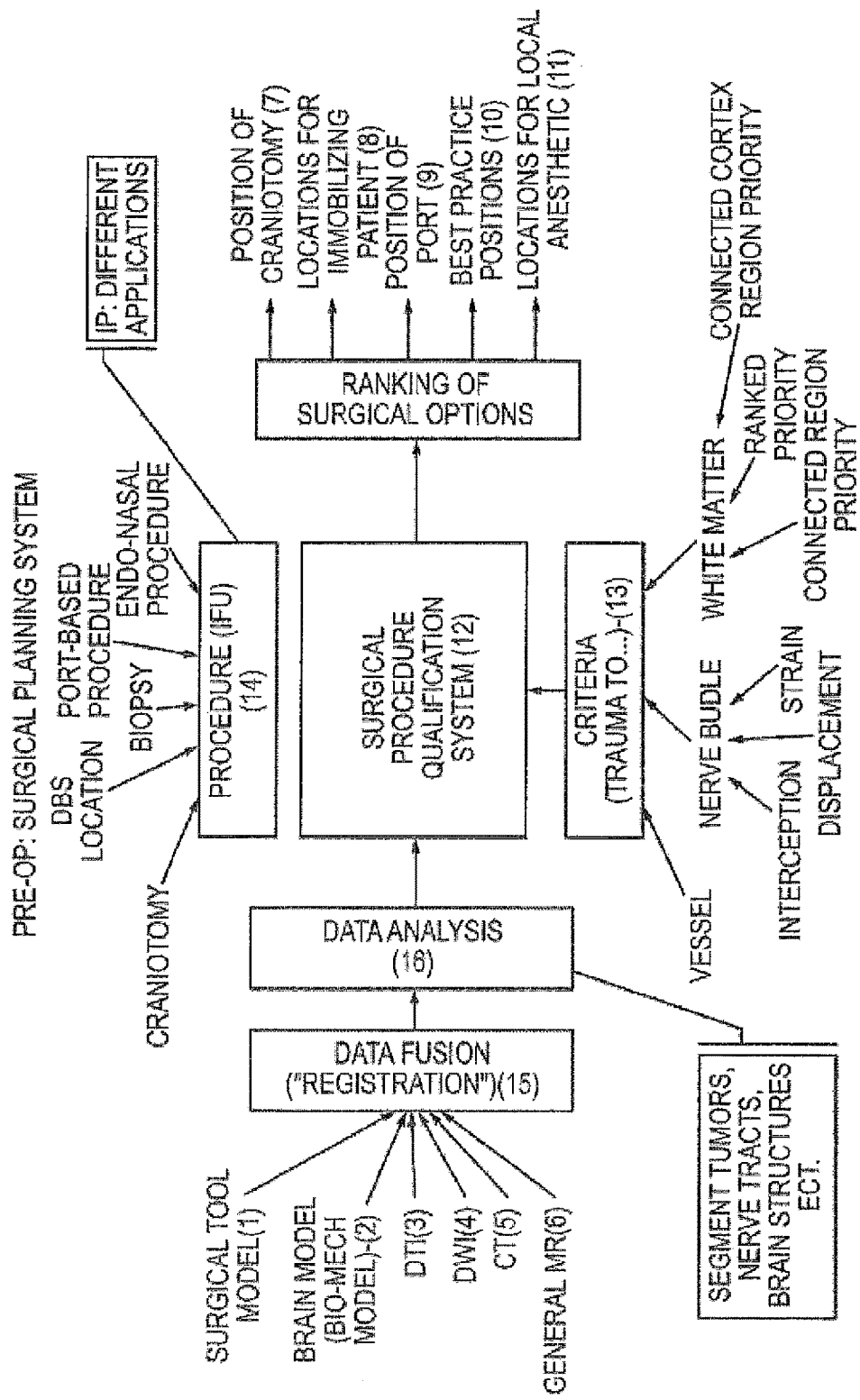
FIG. 1 is a block diagram showing system components and inputs for planning and scoring surgical paths as disclosed herein.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

As used herein, the term "patient" is not limited to human patients and may mean any organism to be treated using the planning and navigation system disclosed herein.

As used herein the phrase "surgical tool" or "surgical instrument" refers to any item that may be directed to a site along a path in the patient's body. Examples of surgical tools may include (but are not necessarily limited to) scalpels, resecting devices, imaging probes, sampling probes, catheters, or any other device that may access a target location within the patient's body (or aid another surgical tool in accessing a location within a patient's body), whether diagnostic or therapeutic in nature.

As used herein, the phrase "optical coherence tomography" or "OCT" refers to an optical signal acquisition and processing method which captures micrometer—resolution, three-dimensional images from within an optical scattering media such as biological tissue. OCT is an interferometric technique, which normally uses near-infrared light. The use of the relatively long wavelength allows it to penetrate into the scattering medium. An advantage of OCT in the context of medical imaging is that it provides tissue morphology images that have a much higher resolution (better than 10 µm) which is currently better than other imaging modalities such as MRI or ultrasound. However, currently OCT is limited to imaging 1 to 2 millimeters below the surface in typical biological tissue, whereas at deeper depths the proportion of light that escapes without scattering is too small to be detected. The images can be obtained 'non-contact' or through a transparent window or membrane but must be in line-of-sight with the target tissue.

As used herein, the phrase "polarization sensitive optical coherence tomography (PS-OCT)" refers to an imaging technique which provides depth resolved measurements of the polarization state of light reflected from turbid media such as tissue. The measurement of the depth resolved Stokes parameters allows determination of the degree of polarization and optical axis orientation in turbid media that can be modeled as a linear retarder.

As used herein, the word "ultrasound" or "US" refers an imaging technique using sound waves in the frequency range of about two to eighteen megahertz. The selected frequency for a particular medical imaging procedure is often a trade-off between spatial resolution of the image, and imaging penetration depth. Lower frequencies produce lower resolution but can image deeper into the body, while higher frequency sound waves produce a higher resolution (due to smaller wavelength, and thus are capable of reflecting or scattering from smaller structures). The higher frequency waves also have a larger attenuation coefficient, and thus are more readily absorbed in tissue, limiting the depth of penetration of the sound wave into the body.

As used herein, the phrase "positron emission tomography" or "PET" refers to a nuclear medical imaging technique directed to generating a three-dimensional image of functional processes in the body. The PET system operates on the principle of detecting pairs of gamma rays which are emitted by a positron-emitting radionuclide or tracer, which is injected into the body. Three-dimensional images of the tracer concentration within the body are then constructed by computer analysis.

As used herein, the phrase "computed tomography" or "CT", also referred to as "X-ray computed tomography" or "x-ray CT" refers to a technology that uses computer-processed x-rays to produce tomographic images (virtual 'slices') of specific areas of the scanned object. Three-dimensional images of the inside of the object being studied may be generated using the technique of digital geometry processing from a series of two-dimensional radiographic images taken around a single axis of rotation. CT scanning of the head/brain is typically used to detect haemorrhaging, bone damage, tumors, infarction and calcifications, to mention a few. Of these, hypodense (dark) structures typically indicate edema and infarction, while hyperdense (bright) structures typically indicate calcifications and haemorrhaging. Tumors are often detectable by the swelling and anatomical distortion they cause, or by any surrounding edema.

As used herein, the phrase "magnetic resonance imaging" or "MRI" refers to a medical imaging technique used in radiology to visualize internal structures of the body and is used to study both anatomy and function in health and disease. MRI is the investigative tool of choice for neurological cancers as it is more sensitive than CT for small tumors. In addition, the contrast provided by MRI between the grey and white matter of the brain make it the leading choice for many conditions of the central nervous system including, but not limited to demyelinating diseases. Furthermore, specialized MRI pulse sequences can be used to give different types of information. For example, "diffusion MRI" is an MRI sequence that measures water molecule diffusion in biological tissues and is clinically useful for the diagnoses of conditions, such as stroke, or neurological disorders, such as multiple sclerosis, and is particularly useful for understanding and visualizing the directionality and connectivity of white matter tracts in the brain. Examples of diffusion MRI are diffusion tensor imaging ("DTI") and diffusion weighted imaging ("DWI"). Also, "functional MRI" or "fMRI", is another specialized MRI sequence that is sensitive to changes in blood oxygenation levels, and can be used to infer areas of increased cortical activity. Typically with fMRI the patient is asked to perform a specified task (e.g. motor activity, cognitive exercise), and the highlighted areas in the fMRI scan can indicate which areas of the brain had increased blood flow (and thus were more active) when such task was being performed.

MRI may also be performed as a perfusion scan, which incorporates the use of a contrast agent (typically Gadolinium) and observes how such agent moves through tissue over time. The typical perfusion scan technique begins with taking a baseline 3d volume, injecting the contrast agent, and then taking repeated scans thereafter (with the patient remaining in the same scanning position during the scan session).

In the above three example MRI techniques (diffusion MRI, fMRI, perfusion MRI), what is generated is a 4d dataset (i.e. 3d volumes evolving over time) which includes data relating to either water diffusion (diffusion MRI), blood oxygenation (fMRI), or a contrast agent moving through tissue (perfusion MRI), in addition to the static imaging data.

In some embodiments the systems and methods can include use of tractography. In the system and methods described herein, the differentiation between tumor and healthy tissue may be performed with DWI sensor(s) and associated processor(s) which use the diffusion of water through tissue of the brain, by Brownian motion, as the primary tissue contrast mechanism. The data acquired from the diffusion contrast scan can be acquired in a predefined gradient direction to enable visualization of diffusion along a specific direction in the brain. This directional information can be used to generate connectivity maps defined by sets of vectors to generate fiber tracts in the brain; wherein these tracts correspond to water diffusing on the outside of the white matter tracts through the brain and correspond to the major nerve fibers in the brain.

The different imaging modalities mentioned above can be combined to give greater insight and more information that can be obtained using only one modality alone. For example, PET scans can be taken in conjunction with CT and/or MRI scans with the combination images (called "co-registered" images) giving better information, and which may include both anatomic and metabolic information. For example, since PET imaging is most useful in combination with anatomical imaging, such as CT, modern PET scanners often include integrated high-end multi-detector-row CT scanners (so-called "PET/CT"). In these machines, the two types of scans can be performed in a side-by-side sequence during the same session, with the patient not changing position between the two types of scans, such that the two sets of images are more-precisely co-registered, so that areas of abnormality observed with the PET imaging modality can be more accurately correlated with anatomy observed from the CT images. This is very useful in showing detailed views of moving organs or structures with higher anatomical variation, which is more common outside the brain.

Thus, as used herein, the phrase "registration" or "co-registration" refers to the process of transforming different sets of data into one coordinate system, and "image registration" refers to the process of transforming different sets of imaging data into one coordinate system. Data may be multiple photographs, data from different sensors, times, depths, or viewpoints. The process of "co-registration" in the present application in relation to medical imaging in which images from different imaging modalities are co-registered. Co-registration is necessary in order to be able to compare or integrate the data obtained from these different modalities. Those skilled in the art will appreciate that there are numerous image co-registration techniques available and one or more of them may be used in the present application. Non-limiting examples include intensity-based methods which compare intensity patterns in images via correlation metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, while multi-modality registration methods are used to register images acquired by different scanner/sensor types. In the present disclosure, multi-modality registration methods are used in medical imaging of the head/brain, as images of a subject are frequently obtained from different scanners. Examples include co-registration of brain CT/MRI images or PET/CT images for tumor localization, registration of contrast-enhanced CT images against non-contrast-enhanced CT images, and registration of ultrasound and CT, to name a few.

It will be appreciated that the planning and navigation methods and systems disclosed herein are applicable to imaging modalities not necessarily currently available. For example, with reference to MRI, new sequences, methods or techniques in addition to those outlined herein may further useful biomedical imaging information, which may be readily incorporated into the methods and systems disclosed herein through an appropriate co-registration technique.

As used herein, the phrase "pre-operative imaging modality" refers to the herein modalities and any other imaging techniques which have the necessary tissue penetration to image anatomy prior to invasive procedures being initiated.

As used herein, the phrase "surgical outcome criteria" means the clinical goal and expected outcome of a surgical procedure as envisioned by a surgeon who is trained in such surgical procedures. In general, the surgical intent of a brain tumor resection surgery is to remove as much of the tumor as possible while minimizing trauma to the rest of the brain and surrounding tissue structures (surrounding tissue structures in this case including any tissue structure that is directly or indirectly affected during the surgical procedure). Examples of surrounding tissue structures to the brain include, but are not limited to, dura, cerebrospinal fluid, and skull.

As used herein, the phrase "point-wise surgical trajectory path" means any continuous (i.e. without breaks) line representative of a path which passes through a beginning point (also known as entry point), a consecutive number of waypoints, and an end point representative of the target, wherein each point is connected to its adjacent points through a curved or straight line defined in 3D space; the path being a representation of the surgical trajectory used to fulfill one or more surgical outcome criteria.

As used herein, the phrase "waypoint" means a point created between the beginning and end points of a point-wise surgical trajectory path with which the path is required to traverse through in a sequence determined by the surgeon to satisfy a surgical intent. In many cases, waypoints are points created to guide the point-wise surgical trajectory path along a desired trajectory. However, waypoints may also indicate points on the trajectory where specific surgical actions may be undertaken. For example, a waypoint may be introduced along a trajectory used in brain surgery to remind the surgical team that a biopsy samples may have to be taken. Alternatively, a waypoint may be used to send a message to a navigation system that parameters may have to be changed. For example, it may be desirable to have an external video scope (automatically or upon user confirmation) switch from a wide field of view during craniotomy, to a narrow field of view during opening of the dura.

As used herein, the phrase "3D image" means a display of an image containing more than two dimensions of spatial information. This display includes but is not limited to, stereoscopic displays, dynamic computer models with an interface allowing for rotation and depth selection, perspective views, and holographic displays. Additionally, it is well known in the field that a 3D image can be represented by a concatenation of 2D images of varying depths or angles therefore reference to a "3D image" is analogous to the reference to a set of distinct 2D images of the same object. It is also possible to create a 3D image directly from 3D measurements in some modalities (e.g. MRI), so the concatenation of 2D images is not normative. Furthermore, the term "volume" and "image" are used interchangeably in this context.

As used herein, the phrase "code segment" means a unit of code executable on a computer such as an algorithm or a program. Embodiments of the present disclosure may include multiple code segments. Code segments are labeled by ordinal numbers, i.e. "first code segment," "second code segment." It should be understood that the ordinal numbers do not signify a specific order with which the code must be executed or implemented nor do they imply interdependence of the programs or algorithms.

While the present method and system may be used for performing surgery on any part of the patient's anatomy, it is particularly useful for performing brain operation procedures as it makes advantageous use of imaging information showing the inferred location and directionality of nerve fascicles and major nerve fiber bundles in the brain. Embodiments described herein are configured to provide a system and method to detect and suggest a surgical corridor to an area of the brain for a given procedure, and predict the potential impact that approach would have on the healthy brain tissue. Such an impact assessment would allow a surgeon to make a decision on approach using quantitative assessment.

For example, there are currently no clinically acceptable means of performing a biomechanical model of brain movement for minimally invasive corridor surgery. Current systems are generally not able to determine the potential movement of brain tissue intra-operatively, to suggest modified approaches to lesions; to suggest modified surgical approaches that would allow more diseased tissue to be resected, while leaving more healthy tissue unaffected; and to evaluate the impact of brain and tissue shift as a result of tissue resection prior to actual resection (as most current scanning and surgical phantoms are contained in a solid container and hence shift in the matrix material is generally minimal). Additionally, there is no means of performing the imaging registration that is required to update pre-surgical plans, with multiple imaging contrast datasets that that provide the appropriate biomechanical information. In other embodiments, a means to manage gross brain displacement, for instance, by way of a small craniotomy access hole and using the natural orifices of the brain allows for simulation approaches to be utilized in manners that can inform surgical approaches in ways not possible with current solutions.

Furthermore, there are no existing planning and training systems that can be used to plan and navigate through brain sulci. There is therefore, a need for surgical planning and training system and method for planning a trajectory along a corridor such as along the sulci, as current moulds for surgical phantoms tend not to emulate the ridge structure present on the surface of the brain.

Also, current training systems generally possess inherent inabilities to fine-tune the training session to the specific surgical scenario, as training is known to be done using an agar gel that is encased in a square mould with a grape located at the centre of the cube near the bottom, which fails to provide the surgeon with a clear understanding of constraints such as inhomogeneity, and orientation and tissue displacement under gravity and pressure. Other embodiments provide for an intelligent system and method which allows for practice of an entire surgical procedure on a simulated platform, which may be useful for performing a mock surgical procedure at least a day in advance of a surgical procedure to identify a patient's head orientation for identification and placement of appropriate surgical tools in advance of surgery. This can be realized through the use of a surgical phantom that closely mimics the brain dimensions of the particular patient and location of tumor model at a geometrically accurate location in the said brain phantom.

The ability to image nerves, and establish surgical procedures to guide devices, or resect tissue while sparing these nerves, requires the integration of navigation technology, software planning systems, pre-operative imaging, and surgical tools. Embodiments of the described system and methods to provide an interface from which a surgeon may plan a minimally invasive approach based on the most up-to-date imaging that is provided for that patient. As nerve bundles, in the context of white matter tracts in the brain, represent a complex data set that may be best represented in a three dimensional context, accurate representations of this information relative to surgical approach provided by the current systems and methods may be critical in order to provide the best possible route to the target of interest. Representing surgical tools and surgical approaches relative to these white matter tracts, and the target of interest (often a complex tumor geometry), has not been addressed in a manner to allow for effective trajectory planning for surgical approaches. In addition, the path for access, is often selected to minimize the amount of grey and white matter that is traversed, without a careful consideration of what the white matter is attached to, (cortical banks of grey matter), or the condition of the white or grey matter, i.e. does it have the chance to recover or is the region eloquent. In addition, the use of natural access corridors in the brain has not been considered in the context of planning.

For instance, the natural folds of the brain, i.e. sulci, offer ideal minimally invasive access pathways to deep locations in the brain. In order to utilize these corridors effectively, a novel software planning system and method are provided to process and calculate input data, represent it to a user, and provide quantifiable metrics to facilitate decision-making.

The systems and methods described herein are useful in the field neurosurgery, including oncological care, neurodegenerative disease, stroke, brain trauma and orthopedic surgery; however persons of skill will appreciate the ability to extend these concepts to other conditions or fields of medicine.

Various apparatuses or processes will be described below to provide examples of embodiments of the planning and navigation method and system disclosed herein. No embodiment described below limits any claimed embodiment and any claimed embodiments may cover processes or apparatuses that differ from those described below. The claimed embodiments are not limited to apparatuses or processes having all of the features of any one apparatus or process described below or to features common to multiple or all of the apparatuses or processes described below. It is possible that an apparatus or process described below is not an embodiment of any claimed invention.

Furthermore, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein.

Also, the description is not to be considered as limiting the scope of the embodiments described herein. Furthermore, in the following passages, different aspects of the embodiments are defined in more detail.

Presented in this disclosure is a software and hardware system to provide diagnostic, surgical planning, surgical guidance and follow-up imaging information to support surgical and image guided therapy procedures. In an embodiment, an exemplary system consists of a computer processing unit, software algorithms, a display unit, input/output devices, imaging modalities, device tracking devices to facilitate medical imaging information representation to facilitate surgical procedures. This system focuses on minimally invasive surgical approaches to managing neurosurgical disease as well as head and neck cancer; however, it is not limited to these applications. These concepts can be used to address diseases throughout the body where minimally-invasive approaches may be coordinated with pre-operative imaging, and/or intra-operative imaging. The system is described in the context of neuro-surgical applications; however the general concept can be extended to various applications described further on in this document.

This disclosure describes methods and systems for pre-operative, intra-operative and post-operative planning and navigation to allow for minimally invasive surgical procedures. The systems and methods may be used as surgical planning systems and methods, or as combined planning and intra-operative guidance and navigation systems and methods, wherein information collected during the surgical procedure is used to guide the next surgical steps, or measure predicted patient outcome.

In an embodiment of the present methods and systems, there is provided one or more sensor(s) which detect input(s), such as pre-operative data input(s) and intra-operative data input(s); the sensor(s) being in communication with one or more processor(s) that receive, record and/or process the input(s) detected by the sensor(s) to generate output(s) that may be useful for surgical planning, navigation and analysis.

FIG. 1 shows an embodiment of the present method and system, for use as a multi-modal surgical planning tool. The system and method can be used as a surgical planning tool in the pre-operative stage. Persons of skill will appreciate that the surgical planning steps depicted in FIG. 1, may also be repeated intra-operatively to further refine the surgical approach, such that the terms surgical planning and intra-operative navigation may be used interchangeably.

In some embodiments, the systems and methods may include data inputs including but not limited to MRI (6), US, CT, other optical imaging systems, and the models of surgical tools (1) and sensors. Imaging data may be acquired by comparing various images of the patient's tissue and organs, including co-registered data between DWI (diffusion weighted imaging) (4), DTI (diffusion tensor imaging) (3), and other imaging contrast sequences and modalities. In an embodiment where the present invention is used in an intra-operative setting, to set or update a surgical path, data inputs may include examples from the above imaging, acquired through sensors, as is further disclosed herein. Sensor(s) may include means for accurately and robustly tracking surgical tools, including optical or electromagnetic intra-operative tracking components, and other means of registration (15) of the intra-operative data sets to the pre-operative dataset. Registration methods can include, for example, any or a combination of the following: image intensity matching based on similarity metrics such as sum of squared intensity differences and mutual information, computed over neighborhoods or regions; image feature based registration such as edge matching; fiducial or anatomical feature based matching of common points defined in multiple image modalities or coordinate spaces (such as a tracking system's coordinate space and an MR image's coordinate space); surface matching techniques such as surface mesh matching.

Surfaces can be manually outlined or automatically segmented from image data. Similarly, surfaces can be determined from the physical patient by outlining with a tracked pointer tool or through a surface scanning technique (such as a laser rangefinder, structured light system or stereo camera). All matching and registration methods can be performed on a sub-region of an image or patient volume (such as what is visualized through the port), to focus on a specific region of interest. Registration can be performed on multiple sub-regions jointly or independently and an interpolated registration can be inferred between these independent regions. Once the images are registered they form an input to a data analysis module (16).

Persons of skill will appreciate that the sensor(s) can also include planning, navigation and modeling components, contextual interfaces, intra-operative imaging devices, devices for bi-polar suction, tissue ablation and tissue cutting with attached imaging, tracking technologies, including external and internal tool tracking (light deflection, capacitive, strain gauge), automated guidance external imaging systems, semi-automated external positioning arms with turrets, internal semi-automated manipulators, multiple beam delivery systems, databases with adaptive learning networks, imaging and spatially linked pathology systems, imaging devices which respond to the context they are used in, as well as user interfaces which respond to the context and environment they are used in.

Inputs and sensor(s) can also include keyboards, touch screens, pointers or tools that act as pointing devices, mice or gesture control components.

The pre-operative data input(s) of the exemplary systems and methods described herein can include pre-operative image data; biomechanical models of tissues and organs; and mechanical models of surgical tools. The intra-operative data input(s) can include images from various modalities including MRI, CT or PET, as well as data from tracking or navigation systems, including tracked surgical devices, such as scissors, ablation devices, suction cutters, bi-polars, tracked access port devices and automated guidance external imaging systems. In some embodiments, particular surgical procedures 14 and clinical criteria 13, selected for example on a patient by patient basis, can be utilized as additional input(s) to assess optimal surgical plans.

In some embodiments, the processor(s) may include planning module(s) 12 that analyze input(s) from 13 and 16 to define surgical approaches. These may include open craniotomies, DBS stimulator locations, biopsy sites, port-based or minimal corridor approaches and endo-nasal based approaches based on a variety of input(s) and rule-based calculations. In further embodiments, the processor(s) may include navigation module(s) that analyze input(s) to provide visualization and other outputs during procedures, such as tool tracking, and contextual information.

In other embodiments, the processor(s) may segment tissue structures such as tumors, nerves and nerve tracts, brain structures, such as ventricles, sulci, cortex, white matter, major white matter bundles, vasculature such as arteries and veins, and boney structures such as skull and brain stem, for planning and navigation purposes.

Output(s) can include 2D and 3D composite images, used for guidance, including tissue extraction guidance and guidance for devices including DBS probes and biopsy probe. Persons of skill will appreciate that output device(s), including monitors or laser pointers can also be included in the systems and methods described herein to provide users with feedback on the processes of the system.

Visualization output(s) can include contextual volume imaging; point source imaging which involves imaging only the regions of interest that are important at that point of the surgical procedure; imaging to check positioning before instrument insertion or removal, imaging to update tissue maps after resection, as well as imaging to resect maximal tumor while limiting damage to healthy or recoverable tissue. In addition, the use of common contrast mechanisms between imaging modalities used in the systems and methods described herein may allow the processor(s) to generate accurate registration between modalities, and meaningful volumetric imaging updates during procedures.

Output(s) can also include path planning or correction data for a surgical approach by way of feature detection, positions for procedures such as craniotomies, locations for pinning and immobilization of patients. Output(s) can also include data on selection of surgical approach, for instance trans-sulcalapproaches to avoid vessels and fiber bundles. For example, the output(s) can also include sulci based approach paths to minimize white matter and grey matter insertion damage. Further output(s) can included parametric curves or volumes to define or facilitate a time evolution of data such as the chosen paths, tissue deformations, time animation of data sets with time components (e.g. Doppler US or fMRI), or arbitrary combinations of such data.

General Planning Method for any Part of a Patient's Body

Disclosed herein is a planning method executed on a computer for planning a surgical trajectory pathway from a surface location on a patient's body to a target location within the body to be approached and operated on. The planning method is quite general and can apply to any part of a patient's body. The method includes acquiring pre-operative images of a portion of the patient's body to be operated on using at least one imaging modality configured for acquiring a 3D image data set or volume and storing the 3D image data set or volume in a storage medium. It will be understood that more than one imaging modality may be used, in particular where the anatomical part of the patient to be operated on would best be suited to a certain type or combination of imaging modality. An image of a 3D volume is produced from the 3D image data set which contains potential entry points into the body along with one or more targets to be approached. The image of the 3D volume is stored the storage medium. Once the location of the one or more targets has been identified, their location(s) may be adjusted and/or confirmed on 2D planar estimates or projections of the data, referred to as "reformats". This technique visualizes representations of one or more 2D planes through the 3D space containing the image data. Such planes are often orthogonal, and often shown in canonical (axial, coronal, sagittal) directions as a "multiplanar reconstruction" or "MPR". Other variants exists, such as "radial stacking" where one or more planes are shown through a common axis about which they all rotate. However it will be appreciated that any configuration of planes, containing image data from a single source or fusions of multiple sources may be used. Where 3D data exists (such as from an MRI, CT, or 3D ultrasounds volume) reformatted images may be produced by interpolating from the sampling lattice with any appropriate standard interpolation scheme. If the desired data is two dimensional in nature (such as an Xray, or 2D ultrasound) the data may be projected onto the reformat plane, or its planar intersection only presented, or both approaches fused as desired. Once the reformatted planes are presented to the user, they may adjust the each planar location within the 3D space, and refine the targeting position relative to each planar representation until they are satisfied that they have identified the correct location in 3D space.

Using the image of the 3D volume, the method includes designating a location of at least one entry point into the patient's body for a surgical apparatus and specifying, from the one or more target locations, a specific target location to be approached. Designation of the location of the one or more potential entry points and target location(s) may be done in one of several ways. For example, the clinician may select the entry point(s) by overlaying a mouse cursor on point(s) of the 3D rendered brain surface and clicking. Alternatively the system may be programmed to automatically select or suggest potential entry point(s), based on a certain criteria (such as the use of sulcal paths for entry). For example, given an image volume (e.g. a T1 MRI image), a segmentation of that image including labeling of portions of the image (into white matter, grey matter, dura, and sulci), and a target, the system could be used to limit or suggest against certain entry locations. The system could generate the best sulcal entry points based on, for example, minimizing the number of impacted fibres, distance from the sulcal boundary to the target, and volume of white and/or grey matter displaced by the approach path. Such points could be found by exhaustive search or various standard methodologies (e.g. energy minimization). A simple approach could be advanced by utilizing additional information (more segmentation labels, biomechanical modelling, fluid dynamic modeling) to apply a more sophisticated analysis to the generation of the "best" candidate points. The surgeon would select from amongst these "best" candidate points, or could reject them and select one manually.

One or more surgical intents or surgical outcome criteria to be satisfied by a surgical trajectory path from the entry point to the specified target location is then selected, and, based on the surgical intent, optionally one or more waypoints between the designated location of the entry point and the specified target location which are consistent with the surgical intent may be selected.

In another embodiment, surgical paths may be traced and recorded through use of a navigation system, while a clinician using tracked tools attempts different approaches toward a target in a brain phantom that has been fabricated to model the actual patient's anatomy.

One or more point-wise surgical trajectory paths from the designated entry point to the specified target location are then computed with the one or more point-wise surgical trajectory paths passing through one or more waypoints between the entry point and the specified target location to define a surgical trajectory path from the designated entry point to the selected target location. These trajectories could be specified manually by a clinician, or they can be computed automatically. An example automatic computation could include the following. Given an MRI T1 image and a surgical entry point and a target specified within it, the system specifies a lattice (e.g. the image voxel centers, or any other lattice chosen for convenience). The lattice infers a graph of connections between all neighboring voxels for a chosen connection scheme (i.e. which may allow only 6-way neighbours without diagonal connections, or 27-way full connections, or any other subset). Each connection is given a weight (i.e cost) base on the pixel intensities integrated along the direct path between lattice points. Now we apply a standard path finding algorithm (e.g. an A* search algorithm, for example Hart, P. E.; Nilsson, N. J.; Raphael, B. (1968). "A Formal Basis for the Heuristic Determination of Minimum Cost Paths". *IEEE Transactions on Systems Science and Cybernetics SSC*4 4 (2): 100-107) to determine the best path. Variants of this approach can include more terms in the cost function based on labeled regions of the brain, biophysical modelling, fluid dynamics, etc. if they are available. Variants may also include post processing of the path (e.g. smoothing) as desired. Waypoints may also be added by the clinician after automatic computation of the surgical trajectory path.

Once the one or more point-wise surgical trajectory paths have been produced they may be stored in the storage medium and visually displayed to the clinician. The one or more surgical intents may be selected by the surgeon checking off from a list of surgical outcome criteria displayed on the computer display screen by overlaying the mouse over the one or more listed intents and clicking them off. Further embodiments may include the use of a touch screen or a stylus, as well as a monitor in connection with a video tracking system or other means of delivering gestural input, or voice input. These surgical outcome criteria will be different for different parts of anatomy being worked on, for example the list of criteria may be different for case of brain surgery compared to spinal surgery.

The step of selecting a surgical intent or surgical outcome criteria to be satisfied by a surgical trajectory path may include selecting one or more anatomical features to be avoided (or to have minimal damage done to them), or alternatively, selecting one or more regions to be passed through by the surgical path, and again this may be done by the surgeon placing the cursor over the particular locations to be avoided or passed through, and clicking the cursor to store such particular location. Once the selection has been made, the locations of the one or more anatomical features is identified from the 3D volume image and one or more surgical paths may be calculated that avoid, or pass through, the one or more anatomical features, as desired. Typical non-limiting examples of anatomical features to be avoided, or to have minimal damage done to them, include any one or combination of nerve damage, muscle damage, ligament damage, tendon damage, blood vessel damage, white matter brain tract damage (in the case of brain surgery).

Identification of such structures can be provided to the system by defining regions of interest, label maps, or other metadata relative to an imaging volume. Alternatively, the system can estimate such structures automatically and use them in other analysis. One method to do this would be by way of co-registering a detailed brain atlas with image volume(s) being used, and then using the atlas labels used as input to the above. Such co-registration may be achieved by constructing the atlas relative to a template clinical image (a representative sample or perhaps averaged image) and then performing co-registration of the template. An example of this is shown in "Medical Image Registration", Derek L G Hill et al 2001 *Phys Med. Biol.* 46 R1. This information can be used as further inputs and constraints to an automated trajectory computation algorithm, such as described previously.

Table 1 summarizes this variation across types of surgery. While it is clear that it is very desirable to avoid many anatomical features, there may be cases where the surgeon does in fact wish to visit and pass through an anatomical feature. Examples of these include deep brain stimulation, resection of multiple tumors, and penetration through a sulcul path.

Structures to be Minimally Impacted

TABLE 1

| Type of surgery | Nerves | Muscles | Ligaments | Tendon | Blood vessels | White matter tracts |
|---|---|---|---|---|---|---|
| Cranial surgery | X | | | | X | X |
| Endonasal | X | | | | X | X |
| Spinal | X | | X | X | X | |
| Orthopedic | | X | X | X | X | |

The method also includes assigning a score to the one or more trajectory paths to quantify how well the one or more trajectory paths satisfy the surgical intent, and based on a comparison of these scores, the best surgical path is calculated. Some non-limiting examples of metrics which correlate to surgical intent for general surgery on any anatomical body part and would be taken into consideration when calculating scores associated with alternate surgical trajectories are listed here:

1. For surgery involving structures such as, but not limited to, nerves, blood vessels, ligaments, tendons, organs etc, the surgical path's incident angle relative to an individual structures may be used to determine the average amount of damage expected to be sustained by the structure, where a steeper incident angle (closer to orthogonal with the structure) would cause more damage and therefore correspond to a worse score than a more parallel incident angle which (closer to parallel with the structure) would cause less damage and therefore correspond to a better score. Further, the number of structures that are expected to be critically intersected can be used as an extension to the metric described herein.
2. The lengths of the surgical paths could also be used to score the trajectories. For example depending on the type of surgical device, its shape and size, longer trajectories may cause the device to apply force over a larger area which may result in greater trauma overall than if the path was shorter. Therefore in this case a shorter path would correspond to a better score whereas a longer path would correspond to a worse score.

3. The number of waypoints used for specifically changing directions could also be used to score. For example if the surgical device is rigid, the higher the number of directional changes that occur the, and the greater the directional change angle(s), the more the tissue is forced to deform. This deformation of the tissue in various orientations with respect to the surgical device may cause additional internal strain and wear on surrounding tissue causing damage thereto. In this manner, a higher number of directional changes, and higher angle(s) of directional change, would correspond to a lower surgical path score. In the case of tumor resection, the incident angle at which the surgical path meets the tumor boundary could also be used for scoring. As a substantially tangential path would be more likely to have the surgical device miss the tumor, slide off the tumor without properly cutting into it, or cause the tumor to roll around relative to surrounding tissue, and thus cause more stress on the surrounding healthy tissue, it should correspond to a worse score. In contrast, to the extent the surgical path is at an orthogonal incident angle when it meets the tumor it will correspond to a better score.

4. In other examples the organs or structures being penetrated by the surgical path may also be taken into consideration for the scoring of the path. In spinal surgery for example, specific ligaments may be ideally not penetrated as they are vital for effective functionality of the joint—the less of these ligaments which are damaged the better the corresponding score of that particular path.

5. The surgical path scores may also be weighted based on statistical data of recovery of the patients derived from previous surgeries within the same context. For example, after a similar path was used (X) times to perform the specific surgery the patient recovery rate was (Z1), in comparison to an alternate path that was used (Y) times where the patient recovery rate was (Z2). In an exemplary embodiment, a "similar path" metric would identify a similar path to the proposed surgical path to be scored, based solely on the anatomic location of the target within a standard atlas (i.e. where a surgeon would describe the location of the target) and the corresponding location of the entry point based on the same atlas. More detail could be added, based either on additional resolution (e.g. definition of the specific location, rather than a more broad anatomic description) or pathology (e.g. the type of tumor), or on detailed statistics or metadata of the surgical path followed (e.g. interaction with anatomical features from an atlas). Other criteria that could be used in assessing a "similar path" would be, the type of tumor being resected from a given path, the specific ligament permeated from a given path, the age of the patient, the location of the tumor, the organs/regions of interest permeated, etc. Therefore shorter recovery time (Z) would correspond to a better score for that particular surgical path.

6. The vicinity of blood vessels to a particular path could also be used to score surgical paths, as the fewer blood vessels (veins and/or arteries) impacted, the lower will be the trauma sustained by the patient. Therefore the lower the number of vessels in the vicinity of the path the better the score.

7. The length of tissue being penetrated could also be used to score the surgical paths, as penetrating through tissue is typically much more traumatic then simply forcing it aside. In this case, paths that require more cutting of tissue would be given a worse score than those requiring less. In addition, the types of tissue being cut or penetrated would also affect the score.

8. Another metric would be the fragility of the tissue being traversed, as in general highly fragile tissues are more likely to suffer damage under manipulation than tougher tissue structures. In this embodiment, an atlas and or a database to derive the most likely values of the specific areas being traversed by the surgical paths in consideration may be used, or else, this information could be derived from direct tissue density or elasticity measurements such as from ultrasound or MR elastography. In yet a further embodiment, tissue fragility may be inferred from known properties of the tissue, including without limitation, its stiffness or rigidity.

These metrics will change depending on the surgical tool being inserted and the surgery being performed. Hence, the score presented to alternative trajectories will incorporate both the type of surgery and specific tools that are planned to be used in the procedure. This also provides the surgeon an opportunity to evaluate the pros and cons of using different surgical techniques and tools for a certain procedure.

The method may also include comparing the scores of the one or more point-wise surgical trajectory paths to a surgical intent score of a path of the shortest distance between the one or more target locations and the closest entry point(s). It is noted that most surgeries currently performed presently use a straight linear path from the surface to the target which corresponds to the shortest distance. Therefore this method performs a score comparison between the more prominently used shortest distance surgical trajectory path and the alternate path being proposed, allowing the difference to be noted by the user for future consideration. In some cases the straight path approach may give the best score in which case, which may also be considered by the user.

The clinician (typically a surgeon) designated location of the one or more potential entry points and target location(s), the first target to be approached, and the surgical outcome criteria are all inputs that may be communicated to the computer by the clinician, and which are all stored in the computer storage device.

It is noted that the present method and system can be configured to be highly automated requiring little input from a clinician. For example, the computer processor may be programmed to determine the locations of one or more surgical targets to be approached by comparing the image of the 3D volume of the patient's anatomy to an anatomical atlas and/or a library of stored images of normal healthy tissue, as described herein. The computer processor may be programmed to select one or more potential entry points and then compute one or more surgical pathways to the first target to be approached and then score each pathway based on a stored set of surgical outcome criteria associated with the particular anatomical part being operated on. The computer then compares the scores and selects the pathway with the best score for the particular set of surgical outcome criteria.

Once the one or more surgical paths have been determined, the surgical/clinician team may wish to run simulations so that the system is programmed to visually display a simulation of the surgical tool approaching the target along the one or more surgical paths and accessing all portions of the target to be engaged by the surgical instrument.

Example Brain Surgery Planning Method

Figure 5:
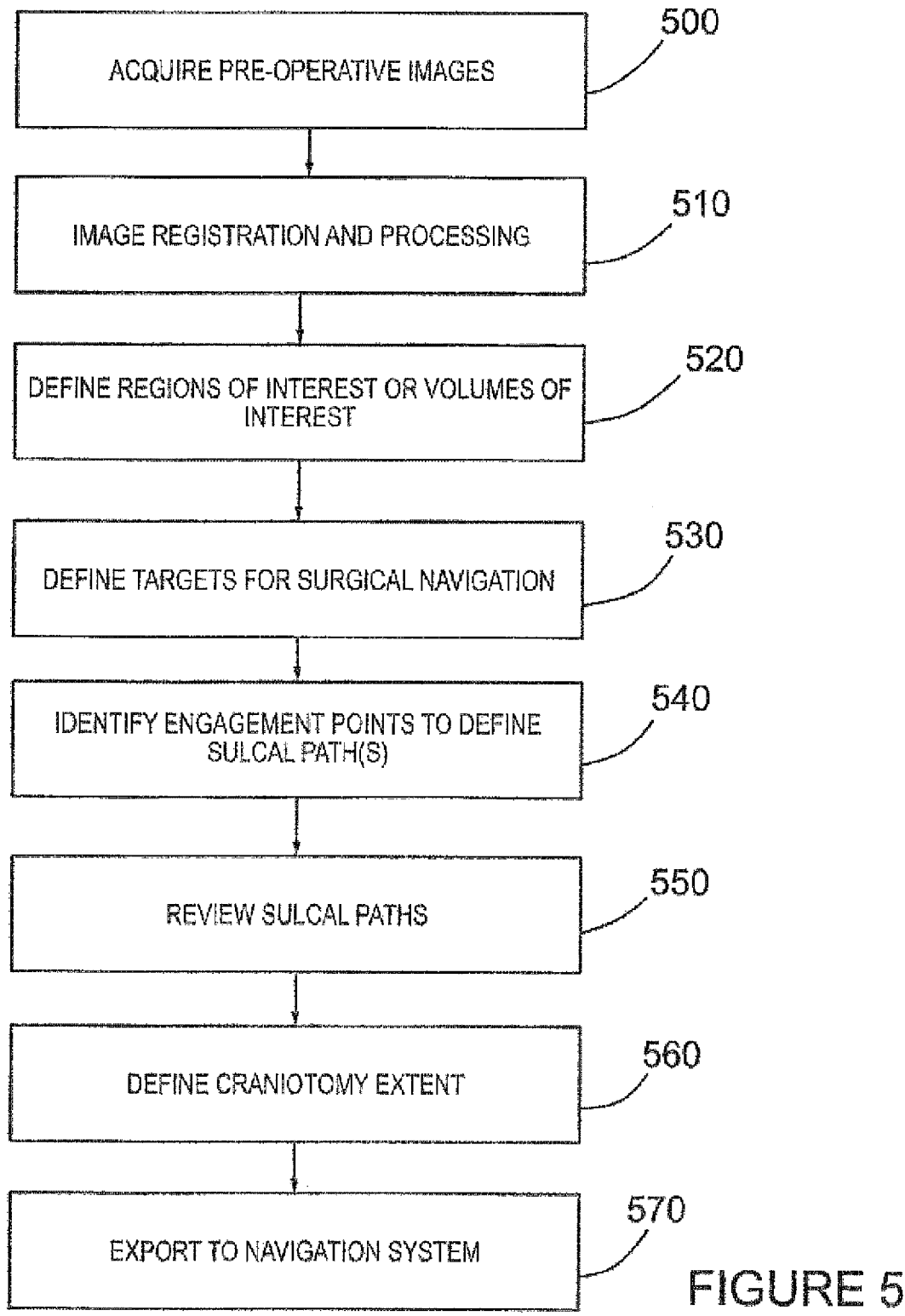
FIG. 5 is a flow chart illustrating the processing steps involved in the planning system and method disclosed herein.

FIG. 5 illustrates the processing steps involved in the planning system using a flow chart. The first step involves acquiring pre-operative images of the patient (as shown in step 500 in FIG. 5). The image data series is first imported into the software from a database or a server, such as a PACS server. The pre-operative surgical planning method and system use pre-operative images (namely those images obtained prior to initiation of the surgical procedure) obtained using at least one, or any combination of, MRI, CT, PET or similar modalities which have the necessary tissue penetration to image the desirable parts of the brain prior to invasive procedures being initiated, and which images typically include fiducials or other markers for orienting the imaging in space.

The present planning method and system can also advantageously use more than one imaging modality. In this situation, the images from the different modalities are co-registered with each other to give combined information. For example, in an embodiment, MRI may be obtained under conditions suitable to acquire both diffusion (typically DTI) data and to obtain MR data useful to generate a 3D sulcal surface map. These pre-operative MR images from which the diffusion images are obtained are co-registered with each other as is also done with the MR images used to obtain the 3D sulcal surface map (as shown in step 510 in FIG. 5) since each MR imaging modality would have its own orientation, geometric scaling and distortions.

As discussed herein, the co-registration process (510) is a common well known process where appropriate transformations are applied to images so that they match each other from a geometric point of view and hence anatomical regions overlap each other in the images obtained using the various modalities. One commonly used algorithm to co-register images is "PET-CT image registration in the chest using free-form deformations," IEEE Transaction on Medical Imaging, Vol:22, Issue:1, (2003). Once the DTI and 3D sulcal surface map are generated, the method involves overlaying of the DTI data onto the 3D sulcal map data. The 3D sulcal map is constructed using the MR data to generate a 3D surface map to represent the brain surface and clearly illustrate the sulcal folds or crevices that are present on the brain. The 3D sulcal map is constructed from the T1 MR image after removing the skull structure from the acquired image. An example algorithm for removing the skull (also known as skull stripping) is provided in "Geodesic Active Contours," Vincent C. et. al., International Journal of Computer Vision 22(1), 61-79 (1997). This overlay of the sulcal map and DTI assists in the detection of co-registration errors since wrong DTI estimates will manifest as protrusion of brain fiber tracts beyond the sulcal boundaries or protrusion into the gyri. Such deviations can be quantized to arrive at a score or metric for quality of co-registration between various imaging modalities. An example algorithm for quantizing the registration error at this stage is as follows: ratio of length of tracts contained in the white matter boundary to the total length of tracts. Ideally, this metric should be as low as possible. One minus this ratio can be used as a goodness measure for assessing the quality of DTI estimation relative to the available brain map.

The process of scoring gives a "goodness of fit" measure between the 3D sulcal map and the DTI data and if the score between the 3D sulcal map and the DTI data suggests an unacceptable amount of registration deviation is present, remedial action will be required to improve the score prior to completing the planning procedure. This remedial action may include re-estimation of tractography data (DTI) using a different starting region that is selected by the user or automatically selected in the vicinity but not overlapping with original seed points. The starting region or collection of points is commonly used in DTI estimation to estimate voxels that collectively represent individual tracts.

A common source of error in DTI estimation is selection of a wrong primary direction for fiber tracts going through a given voxel. The above described selection of a different starting point for tract estimation can force the selection of an alternate primary direction for a given voxel and hence avoid the estimation of a tract that extends into the sulci or beyond the brain surface. It should be understood that DTI estimation is an optimization process and one of many commonly available estimation methods may be attempted to arrive at alternate tracts and the set of tracts that are anatomically reasonable may be retained for subsequent processing. Anatomical correctness of the DTI estimation can be judged by a human reviewer or automated by a software algorithm that estimates the same goodness measure described above while utilizing additional information, such as an anatomical map of the brain that illustrates relative concentration of tracts in known regions of the brain.

This approach may be complicated by the fact the presence of large tumors may geometrically distort the tracts around the tumor region. An inventive aspect of the proposed system is that it can minimize the impact of this distortion on the goodness measure by limiting its estimation to the side of the brain that is least impacted by the tumor. Tumors requiring surgical intervention are often limited to one side of the brain. This information is known apriori since a diagnosis of the tumor(s) would have been completed prior to initiating surgical planning.

After reviewing the processing results using visual confirmation and evaluation of co-registration score, and in the event deviations were found, taking the above discussed steps to obtain overlap data substantially free of unacceptable deviations, specific regions of interest can be defined on one or more images as shown in step (520). Through use of a computer interface the regions can be defined by a clinician on one more 2D image layers, and a corresponding volume of interest can be defined by interpolating between such defined regions. Alternatively, a specific point may be selected by the user to provide an initial estimate of a region of interest (ROI) and a software algorithm may be employed to identify a region in the 2D image layer. A common method to identify such regions is known as connected component labeling. This is described in detail in the following reference and Computer Vision, D. Ballard and C. Brown, that are commonly used in graphics processing.

Alternatively, image segmentation may be employed to establish such ROI. Such ROI may be manually or automatically generated for multiple 2D layers and a volume of interest (VOI) may be established by interpolating in 3D space between such ROI. Again, common techniques such as spline fitting may be employed here. The VOI can be visualized with respect to an anatomical atlas that may be overlaid on the 3D rendered MR, CT or sulcal maps. The ROI and/or VOI may act as landmarks for lesions in need of treatment, or critical regions that must be avoided, during a surgical procedure. In the scenario where ROI or VOI represent a lesion or a region to be resected, the surgeon uses these as target regions. The volume also provides an estimate of the mass of the lesion, tumor or other region that must be resected, which may be useful to a clinician during surgery. Also, intra-operative imaging may be used to assess reduction in volume of the target region throughout the surgical process. In the alternate scenario where ROI or VOI represent regions to be avoided, the surgeon uses these as landmarks where he/she must proceed with caution so as to preserve these regions while still being able to access pathology regions (e.g. lesions, tumors, blood clots, etc.).

Regions to be avoided, in compliance with the desired surgical outcome intent, may be defined as 'no fly zones' for the surgeon to avoid to prevent potential damage to patient's motor, sensory, or any other critical function. Hence, ROI and/or VOI may be defined specifically for a patient based on specific function that would be desirable to be preserved for the patient. Hence, ROI and VOI aid in defining a surgical path that would be uniquely tuned to specific function(s) that need to be preserved for a patient.

Some non-limiting examples of metrics which correlate to surgical intent specific for brain surgery and would be taken into consideration when calculating scores associated with alternate surgical trajectories are listed here:

1. For brain surgery, the surgical path's incident angle relative to the individual fiber tracts may be used to determine the average amount of damage expected to be sustained by the tract, where a steeper incident angle (closer to orthogonal with the tract) would cause more damage and therefore correspond to a worse score than a parallel incident angle which (closer to parallel with the tract) would cause less damage and therefore correspond to a better score. A basic implementation of this would to be take the absolute value of the cosine of the angle between the surgical path and the orientation of the intersecting fibre tract. By way of example, one may assign a score of one for parallel tracts, a score of zero for perpendicular tracts, and set a threshold score under which a nerve fibre tract may be critically intersected. The number of such critically intersected tracts can be used as an extension to the metric described, as, for example, here, a path's score can be divided by or reduced by a function related to the number of critically intersected tracts, thus reducing the score for such paths.

2. For brain surgery, the tracts that are critically intersected by the surgical trajectory can be followed to identify regions of brain that are connected by these tracts. Using this information along with a brain atlas, for example, the functions of the nerve bundles could be determined (i.e. hypothesized) and used to score the path accordingly. In this case, functions that are most suited to be preserved for a particular patient (as determined by the surgeon and patient) would be prioritized and assigned a worse score if intersected, than other neurological functions. For example, preservation of motor function of upper extremities would likely be prioritized over other functions for a professional guitarist. Such regional analysis can be done by a clinician and provided to the system as a series of regions-of-interest or a label image.

3. The lengths of the surgical paths could also be used to score the trajectories. For example in the case of port based brain surgery, longer trajectories may cause the device to apply force over a larger area which may result in greater trauma to the brain than if the path was shorter. Therefore in this case a shorter path would correspond to a better score whereas a longer path would correspond to a worse score.

4. The number of waypoints used for specifically changing directions could also be used to score. For example in a port based brain surgery, given that the port is rigid, the higher the number of directional changes that occur in the path, and the greater the directional change angle(s), the more the brain tissue will be forced to deform. This deformation of the tissue in various orientations with respect to the port will cause additional strain and wear on the impacted surrounding tissue, in particular, the nearby nerves and nerve bundles. In this manner, a higher number of directional changes, and higher angle(s) of directional change, in the port along the surgical path would correspond to a lower surgical path score.

5. In the case of tumor resection in the context of port based brain surgery, the incident angle at which the surgical path meets the tumor boundary could also be used for scoring. As a substantially tangential path would be more likely to cause the port to miss the tumor, fail to engage (slide off) the tumor, or cause the tumor roll around relative to healthy tissue, all requiring more movement of the port and consequently more stress on the surrounding healthy brain tissue, it will corresponding to a worse score. Whereas, in contrast, to the extent the surgical path is at an orthogonal incident angle when it meets the tumor boundary it will result in a better score.

6. The surgical path scores may also be weighted based on statistical data of recovery of the patients derived from previous surgeries within the same context. For example after a similar path was used (X) times to perform the specific surgery the patient recovery rate was (Z1), in comparison to an alternate path that was used (Y) times where the patient recovery rate was (Z2). In an exemplary embodiment, a "similar path" metric would score paths based solely on the anatomic location (as described by a clinician relative to a standard atlas) of both the entry point and target point of the path. Paths that shared both locations or nearby locations according to the atlas would thus be considered similar. More details could be added to make the metric more discriminating. For example additional resolution may be added to the positions (e.g. definition of the specific location in the individual sulcus used for entry), or pathology (e.g. tumor type), or detailed statistics or metadata of the surgical path followed (e.g. percentage of white or grey matter displaced, or interaction with anatomical features. Other criteria that could be used in assessing a "similar path" would be, the type of tumor being resected from a given path, the known mechanical properties of brain tissue in the areas to be impacted, the age of the patient, the location of the tumor, the regions impacted, etc. Therefore, in this example, shorter recovery time (Z) would correspond to a better score for that particular surgical path.

7. The vicinity of blood vessels to a particular path could also be used to score the surgical paths, as less damage to these vessels would clearly reduce the trauma sustained by the patient. Therefore the lower the number of vessels in the vicinity of the path the better the score.

8. In the case of the port based brain surgery the amount and type of tissue being penetrated could also be used to score the surgical paths, as penetrating through brain matter is much more traumatic then simply forcing it aside. In this case penetrating more tissue would give a worse score than penetrating less tissue. In addition, the types of tissue being penetrated would also affect the score. For example penetrating white matter, given its neurological functional importance, would attract a worse score than grey matter, as damage to grey matter is typically less significant (for most cases) to the overall health deterioration caused to the patient by penetration of brain matter. Therefore when penetrating through the same amount of gray and white matter using two different paths, the path penetrating the white matter would give a worse score than the path penetrating the gray matter.

9. Another metric would be the rigidity of the tissue being traversed as highly rigid tissues are more likely to suffer damage under manipulation than more flexible tissue structures. This would require the use of an atlas and or a database to derive the most likely values of the specific areas being traversed by the surgical paths in consideration.

10. Another metric would be to include brain function as part of the path score. Brain function can be measured using functional MRI (fMRI) information (BOLD contrast imaging), Magnetoencephalography (MEG), Raman Spectroscopy, or electrophysiological measurements. Paths through regions with high levels of function, a higher ranking of brain function hierarchy (regional importance), or which are functionally related to such regions, would all have a worse score. Furthermore, paths through white matter tracts connecting such functionally related regions would also have a worse score.

11.

Once regions of interest are defined, one or more targets may be identified in the images (as shown in step 530). Targets correspond to a three dimensional location within the brain that must be accessed to resect the tumor (or lesion). It is known that to accurately spatially locate a point in 3D space, a minimum of three orthogonal planes are necessary. However, additional views may be presented where these additional views contain images obtained using different modalities. In other words, the additional planes may geometrically overlap with the above mentioned orthogonal planes and present images captured using other modalities that complement the modality presented in the aforementioned three orthogonal planes. For example, the three orthogonal planes may represent T1 MR image slices while additional views may present co-registered images obtained using CT or B0 (another MR data representation). The complementary modalities aid in confirming the location and extent of tumors or blood clots. Another redundant means of presenting information to aid in estimation of tumor location is presentation of data as radial slices where virtual slices are generated such that the slices are along the planes that are situated radially about a user-defined axis.

Figure 7:
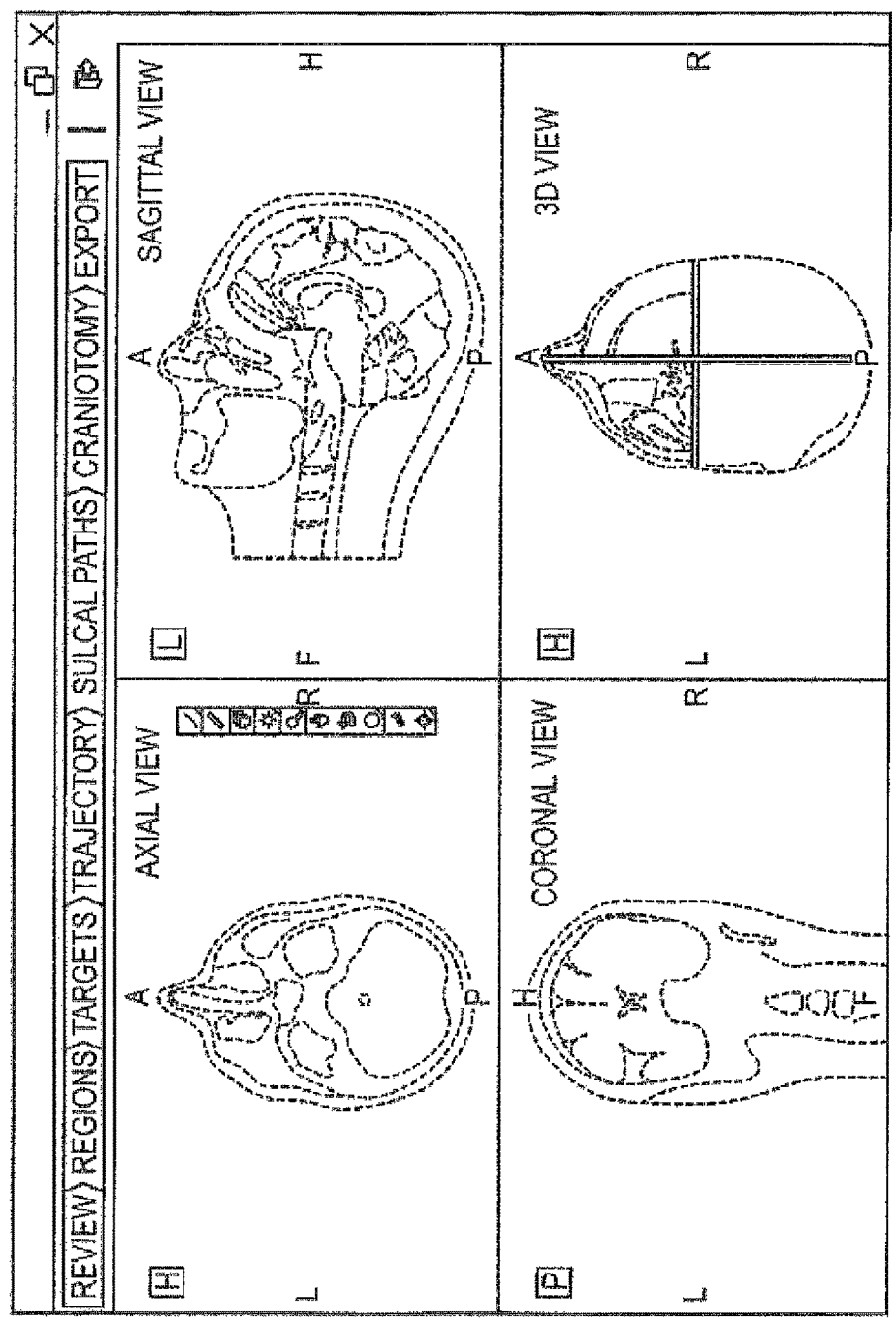
FIG. 7 shows an output of an embodiment of the present method and system showing visualization patient anatomy using three orthogonal projections. The two display panes in the top row and left most pane in the bottom row illustrate 2D projections that are orthogonal to each other.

Visualizing the target being operated on in multiple 2D images mitigates the risk inherent in placing the target in 3D space only using a 3D rendering of the brain (see FIG. 7). This latter approach is prone to errors because the 3D surface is rendered on a 2D display. It should be noted that a 3D holographic display may also be used to overcome this risk since the surgeon will have the ability to view the 3D virtual object from multiple perspectives to confirm the location of the target. In an embodiment, this can be used as an alternative to presenting image data in three orthogonal planes.

Another inventive aspect of the invention is the ability to visualize white matter tracts that are in the immediate vicinity of the target. This functionality is achieved by hiding diffusion tracts (or tractography information) in all regions of the brain except for the tracts that intersect the geometric space occupied by the target region or within the immediate vicinity (within a threshold). Alternatively, the tracts that intersect the geometric space occupied by a surgical tool that is virtually inserted in the brain may be displayed. Such tool may be a virtual representation of a biopsy needle, a port for minimally invasive surgery (e.g. an access port), a deep brain stimulation needle, or a catheter, to name a few. This approach of selective display of DTI information helps manage the large-data problem associated with visualization of an entire DTI image. It also aids the surgeon in narrowing their focus and seeing principally the impacted tracts, as opposed to all tractography information associated with the entire brain. This selective filtering of renderings of white matter tracts in the immediate vicinity of the target region, or those which are expected to be impact by a tool, will allow the surgeon to view tract information within a selectable degree of translucency in order to aid in the selection of surgical paths which may best meet the surgical intent. Furthermore, such selectable display of DTI information could similarly be replaced or supplemented with any other co-registrable modality, including fMRI or other modalities which are able to assess brain functionality that may be potentially impacted during tumor resection. See FIGS. 8 and 9 for illustration of tract intersection visualization.

The system may be programmed to provide a histogram analysis, in which there is computed a histogram of the number of fibers that would be displayed versus the threshold shear cut-off angle. This provides information on the sensitivity to this threshold. In one embodiment, the software could suggest an alternate cut-off angle near the set cut-off if there is a value where the number fibers that would be displayed suddenly jumps, i.e., where there would be a big change in display given a small change in cut-off threshold.

Alternately, instead of a binary cutoff threshold the display could be modulated so to provide a gradation of fibers displayed (e.g. by reducing fiber intensity or increasing transparency) as the intersecting angle increases beyond the set threshold or between minimum and maximum set thresholds.

Another embodiment may involve distance analysis where the system and method are configured to display only a set distance of each tract from its intersection with the port rather than the full path of the tract, as fibers that are further from the intersection point are less likely to be impacted. This distance threshold can be adjusted and manipulated dynamically. The display of each tract can also be modulated by distance from port intersection (e.g. by decreasing brightness, changing color, increasing transparency or decreasing displayed tract thickness with distance).

Alternately, the displayed tracts can be similarly modulated by the distance of intersection with port to an endpoint, as tracts that are impacted at or near their end-points are potentially less affected than tracts impacted further along their trajectories.

The next step in establishing a surgical path is the identification of the entry point, which is also known as an engagement point (as shown in step 540). It is noted that this entry point refers to the entry point of the leading section of the surgical port tool into the dura of the brain. There may be another entry point of the surgical port into the white brain matter. The first entry point mentioned above is established by visualizing the sulci with the overlay of a virtual access tool, such as a port tool, biopsy needle, catheter etc. However, an advantage of the current invention is that the virtual port tool may presented in such approaches in an unobstructed manner by representing it as a translucent model of the tool.

The target and the engagement points can be then used as navigational benchmarks to define a sulcal path (as shown in step 550). In an embodiment the present method and system is configured to define a piecewise linear sulcal path that includes the engagement and target points as the two extreme beginning and end points respectively in the surgical path and additional spatial locations between the two extreme points. These additional spatial location points may be inserted to define a piecewise linear path when turns are observed in the sulci. The piecewise linear path that closely follows the turns in the sulci may optimally preserve the regions of the brain that are contacted by the surgical tool where such surgical tool is of low profile, and/or flexible or articulated. Hence, an articulated or flexible port can be anticipated to utilize such piecewise linear path to further reduce trauma to the brain. A metric or score can be associated with a specific sulcal path to indicate the extent of brain tracts that are intersected by the virtual port. Hence, the score can be used as a measure of trauma expected to be introduced by the port when using the planned sulcal path. In other words, the number of intersected tracts may be used to compare two or more different paths to identify the path that presents the minimal number of tract intersections.*

Finally, alternative location and geometry for craniotomy can be evaluated by modelling surgical tools and assessing the range of motion available for each tool when the tool's motion is constrained by the dimensions and location of the craniotomy (as shown in step 560). This range of motion may be seen in FIG. 10. Further, the craniotomy location and the sulcal path can be more accurately visualized by radially stacking the image slices. In other words, the 3D reconstructed MR image of the whole brain can be used to make virtual 2D image slices that share a common axis that is reasonably close to the planned sulcal path. Such slices expose the extent of sulci close to the planned path and hence assist in better visualization of alternative sulcal paths. A final scorecard is created to present all the metrics from each of the preceding stages and a metric to represent goodness of fit for each of the defined sulcal paths. The goodness of fit for the sulcal path (also known as sulcal correspondence percentage) is the ratio of the planned trajectory and the sum of total length of the described sulcal path plus the Euclidian distance from the end of the path to the target. This ratio is then multiplied by 100 to express the ratio as a percentage. This metric indicates the correspondence between the linear trajectory and the chosen sulcal path. One hundred percent means perfect match or linear path.

The established surgical plan is then stored and/or exported to a navigation system (570) that can typically receive such data and store and/or co-register (if necessary) such plan or surgical path for the surgeon to use in navigating his or her surgical tools during the surgical procedure. An inventive feature of the planning system allows the surgeon to visualize the entire procedure and compare alternative surgical plans by automatically playing back the surgical steps as a video. This aids the surgeon in visualizing the entire procedure and hence serves as a confirmatory step and as a training step for the surgeon.

If the medical procedure is to address a dire medical emergency and there is no time to obtain images from multiple imaging modalities, then the present method and system may be configured to use a single non-invasive imaging modality. In this situation the planning method for planning a pathway from a sulcus to a location in a patient's brain to be operated on includes acquiring pre-operative images of a patient's brain to be operated on using a non-invasive imaging modality and co-registering the pre-operative images. The co-registered images are used to identify a sulcal structure of the patient's brain and one or more targets and associated one or more target locations to be approached and operated on during the invasive surgical procedure. The one or more target locations may be visually displayed in at least three orthogonal planes to confirm the location of the one or more targets in 3D space. Based on the location of the entry point and the one or more target locations, there is defined a piecewise linear surgical path with the location of the entry point and the location of a selected one of the one or more target locations being designated as beginning and end points respectively in the surgical path. The surgical path is selected to avoid passing through selected anatomical features of the brain.

After the planning stage has been completed and the surgery has started, and once the brain tissue is visible, other imaging modalities that could not be used to acquire intra-operative images may then be used to acquire intra-operative images in addition to the above mentioned MRI, CT and PET modalities. Such modalities include OCT, PS-OCT, ultrasound etc. These will be discussed in more detail hereafter during discussion of the navigation part of the surgical procedure.

Figure 2:
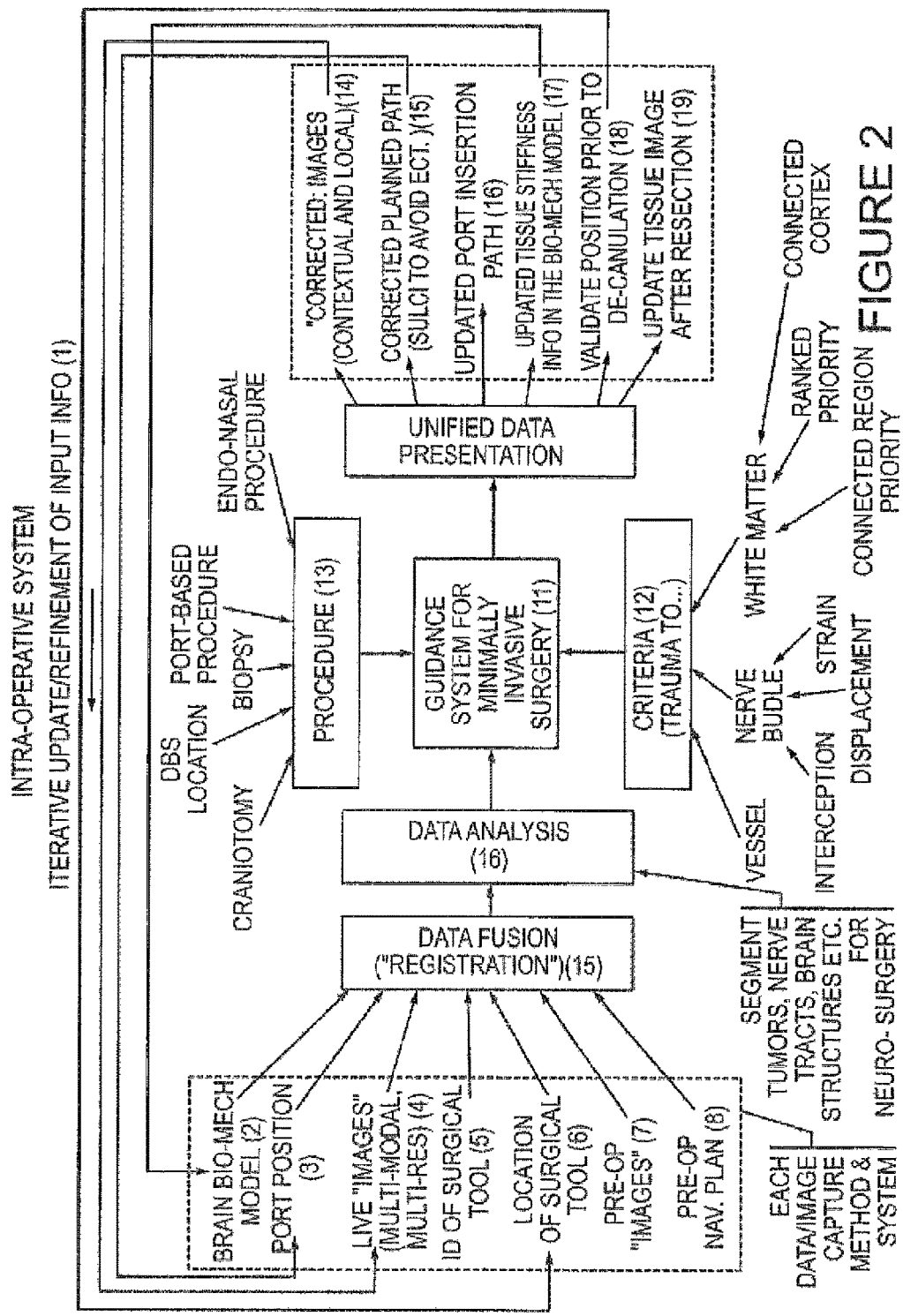
FIG. 2 is a block diagram showing system components and inputs for navigation along the surgical paths produced by the planning system of FIG. 1.

FIG. 2 shows an embodiment of the present method and system, for use as an intra-operative multi-modal surgical planning and navigation system and method. The system and method can be used as a surgical planning and navigation tool in the pre-operative and intra-operative stages. Persons of skill will appreciate that the data input(s) of the surgical planning steps and surgical procedures described in FIG. 1, can be used as input(s) to the intra-operative navigation stage described in FIG. 2, through the use of patient fiducial markers visible in the imaging, or other imaging techniques, examples of which are known in the art.

The embodiment of FIG. 2 provides a user, such as a surgeon, with a unified means of navigating through a surgical region by utilizing pre-operative data input(s) and updated intra-operative data input(s). The processor(s) of system and methods are programmed with instructions/algorithms 11 to analyze pre-operative data input(s) and intra-operative data input(s) to update surgical plans during the course of surgery. For example, if intra-operative input(s) in the form of newly acquired images identified a previously unknown nerve bundle or brain tract, these input(s) can, if desired, be used to update the surgical plan during surgery to avoid contacting the nerve bundle. Persons of skill will appreciate that intra-operative input(s) may include a variety input(s) including local data gathered using a variety of sensor(s).

In some embodiments, the system and methods of FIG. 2 may provide continuously updated intra-operative input(s) in the context of a specific surgical procedure by means of intraoperative imaging sensor(s) to validate tissue position, update tissue imaging after tumor resection and update surgical device position during surgery.

The systems and methods may provide for re-formatting of the image, for example, to warn of possible puncture of critical structures with the surgical tools during surgery, or collision with the surgical tool during surgery. In addition, the embodiments disclosed herein may provide imaging and input updates for any shifts that might occur due to needle deflection, tissue deflection or patient movement as well as algorithmic approaches to correct for known imaging distortions. The magnitude of these combined errors is clinically significant and may regularly exceed 2 cm. Some the most significant are MRI based distortions such gradient non-linearity, susceptibility shifts, eddy current artifacts which may exceed 1 cm on standard MRI scanners (1.5 T and 3.0 T systems).

Persons of skill will appreciate that a variety of intraoperative imaging techniques can be implemented to generate intra-operative input(s) including anatomy specific MRI devices, surface array MRI scans, endo-nasal MRI devices, anatomy specific US scans, endo-nasal US scans, anatomy specific CT or PET scans, port-based or probe based photoacoustic imaging, as well as optical imaging done with remote scanning, or probe based scanning.

Figure 3:
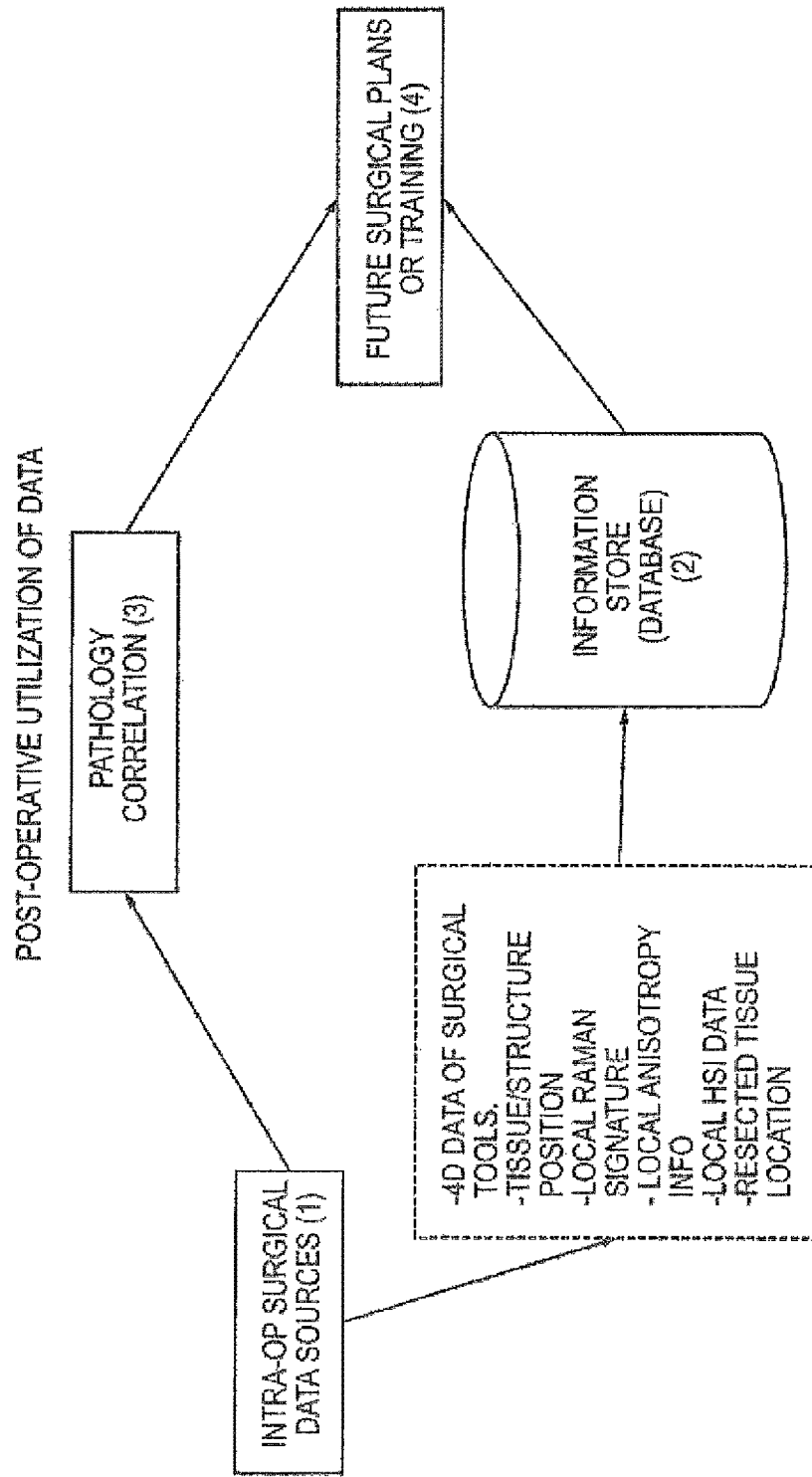
FIG. 3 is a block diagram showing system components and inputs for post-operative data analysis.

FIG. 3 shows an embodiment of the present method and system for post-operative data analysis. As shown in FIG. 3, the input(s) and output(s) 1 captured during the pre-operative and intra-operative stages of the methods and systems described herein, may be used for analysis of future surgical procedures and training purposes. Vast amounts of data captured during pre-operative and intra-operative stages can be used for future surgical procedures and training purposes.

In such an embodiment, the system may include dedicated database(s) 2 for storing and retrieving input(s), output(s) and processor(s) activities. The database 2 may include data for recovery analysis, outcome assessment, therapy planning, pathology correlation 3, future surgical plans and/or training 4 and cost validation (health outcomes v. economic metrics).

Persons of skill will appreciate that the input(s) and output(s) captured by the system and method may include data on the use of surgical tools, continuous recording of tissue during surgical procedures using local, imaging scans, local raman spectra, local anisotropy information of tissues to illustrate morphological structures, local hyperspectral image data of tissue to aid in tissue differentiation, spatial location of resected tissue for correlation with specific regions in the body, and pathology information inferred by a pathologist or radiologist for aiding future surgical procedures or training purposes.

The information accumulated during the pre-operative and intra-operative stages can be effectively utilized for future surgical planning for the same patient, gathering clinically relevant information for pre-operative surgical planning for other patients and/or training purposes as illustrated in FIG. 3.

As the systems and methods disclosed herein may generate a large volume of data to be captured, in some embodiments, input and output data may be communicated to additional system components, for example, for remote review of the data by users located at remote locations.

In further embodiments, surgical procedure and clinical criteria, selected for example on a patient by patient basis, can be utilized as additional input(s) metrics to assess optimal surgical plans. Additional metric input(s) can include minimal trauma trajectory to location of interest, such as minimized vessel trauma, minimized nerve bundle trauma or prioritized nerve bundle trauma. Metric input(s) can include, for example measured or predicted trauma to brain tissue, including damage to white matter, damage to regions connected by white matter, damage to regions of the cortex connected by white matter, and damage to vessels on approach.

In some embodiments, input metric(s) may include angle of contact between tissue and instruments as well as trauma to nerves and connected fibers, which may be measured by interception or displacement of tissue with instruments from both historical and surgical data.

Additional input metric(s) may include: position of device to be tracked relative to tissue of interest by tracking technologies; geometry of surgical devices and ports; anticipated positioning of instruments and ports during surgery; best practice locations for immobilization of patient anatomy, such as the head band region for the Mayfield clamp; and locations for associated procedures, such as the administration of local anesthetic. Persons of skill will appreciate that input metric(s) can be associated with particular approaches, diseases or procedures, and that these metrics can be both user selected and automatically generated.

In further embodiments, processor(s) may be used to perform imaging artifact, or anomaly, correction to represent structures and targets in accurate positions. Gradient non-linearity correction, susceptibility shift correction, eddy current artifact correction and pixel interpolation error corrections are examples of processes that may be performed by the method and systems to correct for artifacts in the images, post-acquisition, and to provide high quality and accurate representations.

In still further embodiments, the systems and methods may include co-registration components and techniques to align various imaging modalities and varying scans within a modality. Registration may performed on images acquired by numerous types of sensor(s) including MRI, PET, CT, US, Optical imaging, such as surface scanning and spectroscopic techniques and photo-acoustic imaging.

In still further embodiments, the systems and methods may be configured to direct sensors to particular regions of interest in the patient's body, to produce high quality images intra-operatively that focus on specific areas of interest, specifically, the area of the desired surgical field or point at the appropriate time during the surgery. Implementation of such surgical field imaging may be achieved by the system through the use of appropriate scale of imaging or contrast mechanisms, for example. By focusing the imaging on a specific location of interest, the signal to noise can be improved by multiple factors, and new imaging contrast mechanisms can be utilized.

In some embodiments, the system and methods may generate as output(s) minimally invasive approaches, based on the processor(s) analysis of the input metric(s). For example, input metric(s) may be weighted to generate patient or procedure specific output(s). The processor may to rank various surgical alternatives presented by a surgeon or various surgical alternatives may be automatically generated by the system using adaptive learning paradigms, such as decision trees and neural-networks.

In some aspects of the present methods and systems, there is provided systems and methods to integrate surgical instrument and port specific information, such as size, shape or impact on nervous tissue with data on the patient's anatomy to qualify user selected port approaches. For example, input(s) including properties a subject's nerve fascicles, nerve bundles, sulci and gyrus patterns, vessels, skull and skull-base can be used to assess the surgical instrument or port insertion's impact on the nervous structures of the brain. In some embodiments the systems and methods can provide for surgical instrument and port planning to determine an appropriate craniotomy, incision, head-holder, external imaging devices and location of equipment in the operating room based. These systems and methods may lead to less invasive, more accurate and faster insertion device or port based surgical procedures, with improvements to patient and economic outcomes.

In some embodiments, the systems and methods disclosed may include as input(s) data on the fibers, sulcus and gyrus structures of the brain, in addition to other input(s) such as tumor location. These input(s) may be useful in determining paths or locations of surgical device insertion, for example. In some embodiments planning output(s) may include device insertion paths into the brain through natural orifices such as sulci. In other embodiments, input(s) such as tumor databases in addition to other input(s) such as tumor location, can be included.

In some embodiments the systems and methods can include tractography input(s). In the system and methods described herein, the differentiation between tumor and healthy tissue may be performed with DWI sensor(s) and associated processor(s) which use the diffusion of water through tissue of the brain, by Brownian motion, as the primary tissue contrast mechanism. The data acquired from the diffusion contrast scan can be acquired in a predefined gradient direction to enable visualization of diffusion along a specific direction in the brain, represented in FA maps that provide information about the general directionality of diffusion throughout the image. The processor(s) can use this directional information to generate connectivity maps defined by sets of vectors to generate fiber tracts in the brain; wherein these tracts correspond to water diffusing on the outside of the white matter tracts through the brain and correspond to the major nerve fibers in the brain.

For example, the systems and methods may include diffusion contrast imaging devices to generate DTI images, and measure the Fractional Anisotropy ("FA"), and Apparent Diffusion Coefficient ("ADC") of tissue. The ADC, which measures the magnitude of diffusion, and the FA which measures the general directionality of diffusion throughout the image, can be used to identify major fiber tracts through the brain, measure increased cellularity associated with tumors, measure diffuse or local traumatic brain injury and white matter disease associated with neurodegenerative disorders.

Through the combination of ADC, FA maps and DTI images the systems and methods can measure major fiber tracts through the brain, measure increased cellularity associated with tumors, measure diffuse or local traumatic brain injury and white matter disease associated with neurodegenerative disorders. For example, to perform a craniotomy to resect as complete of a tumor margin as possible, the multitude of MRI contrast mechanisms can be used to define tumor boundary, define critical structures in the brain, define functional areas, and define an approach to tumor resection.

Figure 4A:
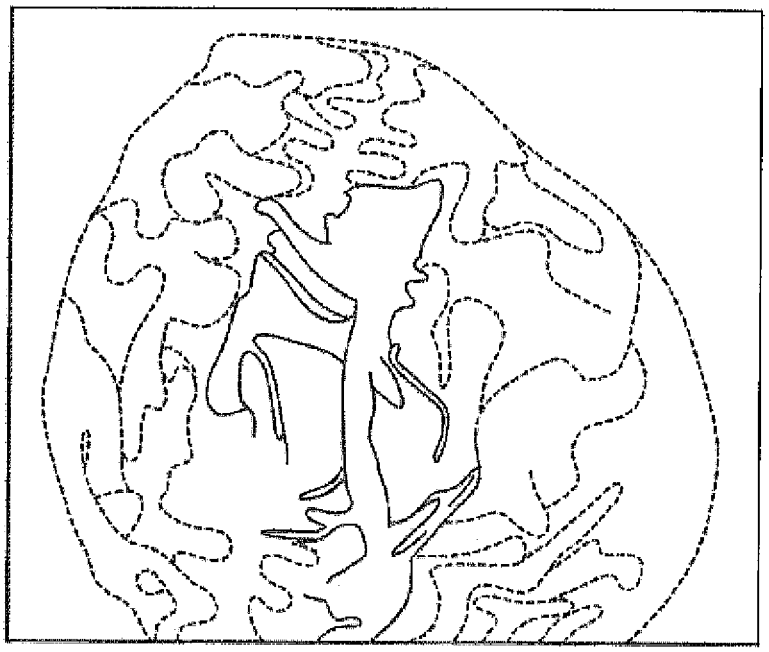
FIGS. 4A and 4B shows an embodiment of the present method and system, wherein processor(s) have identified fiber tract bundles to aid in optimal selection of surgical approach.
Figure 4B:
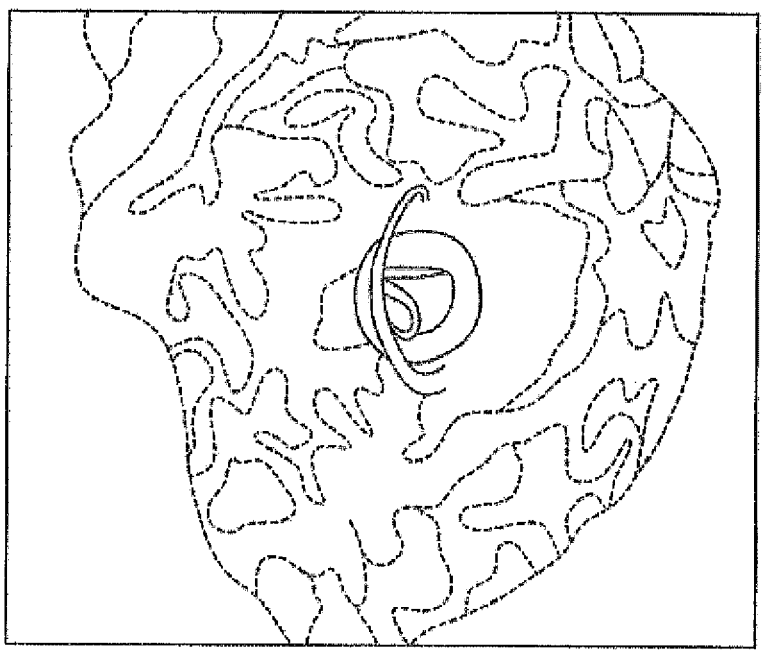

FIG. 4 shows an output(s) of an embodiment of the present method and system, wherein processor(s) have identified fiber tract bundles for optimal selection of surgical approach. In the embodiment shown, output(s) may include locations and visualizations of trans-sulci pathways which may provide for avoidance of blood vessels and fiber bundles. The output(s) may visualize and track surgical approaches to minimize white matter and grey matter insertion damage.

In some embodiments, the methods and systems disclosed herein may include as input(s) ranking information of fibers and tissues.

In some embodiments, the current systems and methods are configured to identify minimally invasive corridors, for example through sulci, based on input(s) such as the sum total of all of the white and grey matter information available by the system, which may be used to calculate a minimally invasive pathway. For example, given an MRI T1 image with segmentation into white matter, grey matter, sulci, and CSF, etc., and a surgical entry point and a target specified within the information, the system specifies a lattice of the image voxel centers and forms a graph of the 27-connected direct voxel neighbors. Each connection is given a weight based on the voxel label as white matter, grey matter, sulcus, or other. Weights are chosen to reflect the relative preference of impacting one tissue type over the others (which may be determined by a clinician). A path finding algorithm (e.g. A* search algorithm, as noted above) may be used to determine the path of least total impact to tissue. Further embodiments may represent the surgical instrument(s) in a realistic manner relative to, and interacting with the represented tissues, and to represent the biomechanical properties of tissue to simulate tissue distortion, as each path is attempted. Further embodiments may integrate additional imaging and outcome information to support clinical decision making for the approach.

The system and methods may generate and plan a minimally invasive corridor through several different embodiments, such as 1) planning without using a deformation model, 2) planning using a deformation model, or 3) planning using intra-procedure imaging to update information, in the context of a deformation model. An exemplary method of producing a deformation tissue model is disclosed in copending PCT Patent Application Serial No. PCT/CA2014/050243 entitled SYSTEM AND METHOD FOR DETECTING TISSUE AND FIBER TRACK DEFORMATION, which is incorporated herein in its entirety by reference.

In an embodiment, the system and method may be configured to function on the assumption that the tissue will not deform when the port is inserted into the tissue. The system and method in this embodiment may be configured to generate minimally invasive corridor outputs with a fixed set of imaging data. Clinically, although this may be a reasonable assumption, during port surgery for example, a port will generally follow the sulci, and the sulci will pull, or compress the underlying tissue.

To generate and plan a minimally invasive corridor, the system and methods are configured and programmed to select a target of interest, which may be represented as an overlay of contrast uptake information, diffusion weighted maps (ADC), T2 changes, or a combination of these and additional contrast, for instance. This target may be a user input, for example, or can be generated by the system and method based on existing data or images. When the system and method have identified the target of interest (such as a point on 3D image set), a representation of the access port that is selected by the user may be shown on an output or feedback component of the system and method, such as a screen.

During port surgery, for example, the system and method may fix the port into position, for example at the tip of the lesion, which may be rotated around the point in three-dimensions. The line of entry of the port and its axis of insertion define the approach taken into the brain, subject to the system and methods selecting a corridor wherein entry occurs on a single linear trajectory, not multiple linear trajectories, or curved trajectories.

The systems and methods disclosed herein may provide for virtual insertion and removal of the port, or other surgical tool, into the brain tissue. As it is inserted, the registered set of DTI tracks that make contact with the tip, and outer surface of the port may be identified by the system and method through a ray-tracing, or similar calculation. If the fibers come into contact with the port at an angle of 90 degrees, the system and method may predict that these are the most at risk of shear or tear from contacting the port; however, if they run parallel, the system and method may detect that they are at the least at risk of shear or tear. In some embodiments, the system and method may set a threshold (for example, an angle of over 60 degrees) which may suggest damage to the nerve fiber. This threshold can be modified by the surgeon in practice, and when set, may allow for an inference of all nerve fibers that are at risk during a procedure.

Further embodiments can provide visualization tools to assess the effects of different potential shear angles between intersected fibers and the inserted port. These tools can include the display of a computed histogram of the number of fibers that would be at risk of shear versus the shear cut-off angle. Such tools can provide information on the sensitivity to this threshold. The embodiment can also be configured to suggest an alternate cut-off angle near the set cut-off if there is a value where the number of displayed fibers suddenly jumps—i.e. where there would be a big change in display given a small change in cut-off threshold. Alternately, instead of a binary cut-off threshold, the embodiment can also be configured so that the display could be modulated so that there is a gradation of fibers displayed (e.g. by reducing fiber intensity or increasing transparency) as the intersecting angle increases beyond the set threshold or between minimum and maximum set thresholds.

A further embodiment can show only a set length of each fiber tract from its intersection with the port rather than the full path of fiber, as fibers that are further from the intersection point are less likely to be impacted by the port insertion. This length threshold can be adjusted and manipulated dynamically. The embodiment can also be configured to have display of each fiber modulated by distance from port intersection (e.g. by decreasing brightness, changing colour, increasing transparency or decreasing displayed fiber thickness with distance). Alternatively, the display fiber can be similarly modulated by distance of intersection with port to a fiber end-point, as fibers that are impacted near their ends are potentially less affected than fibers impacted further along their trajectories, in other embodiments.

To provide a user with a visualization of nerve fibers within the context of the rendering volume, the system may outline the impacted nerve fibers in black, such that the black lines can be projected through the 3D rendering, for example. In addition, the system may display a thin slab of the rendered DTI data volume, such that this slab may be moved along the axis of the port on the output devices to display the impacted fibers at various depths along the port. In addition, looking coaxially down the port, for example, all of the fibers that contact the port may be shown as a rendering on the output devices of the system and method.

Furthermore, as a means to reinforce a port based approach, the system and method may represent the port as a fixed visualization mode, such that the brain and tissue beneath the port may be moved relative to the port, on an output device or display. This may provide a visual means of finding an appropriate, least impactful path to the point of interest.

Additionally, the system and method may identify a frame of reference at the targeted point within a target, such as a tumor. This may provide a user with "inside looking out" view which may be beneficial for visualization of possible pathways to the tumor by identifying openings through the path to the surface. This may be used as an alternative or complementary means of the system and method's use of rendering to identify a path.

In some embodiments, the system and method may model a surgical instrument, such as a port, as a larger or smaller diameter in order to determine whether a different port size can be used for a particular procedure, or the sensitivity of an approach to variations in the procedure, such as mis-registration of data-sets, in-accuracies with navigation of the port, or movement of tissue during the procedure. In addition, the port target point may be shifted by the system and method to determine the impact on the sensitivity of the approach.

In some embodiments, in addition to finding the least impactful approach relative to the fascicles and nerve bundles, the system and method can tend identify the sulci as a preferred access route to the brain. In such embodiments, the surface rendering of the tissue may be used by the system and method to identify these natural orifices. This may constrain the output trajectories to only those trajectories that insert at sulci at the surface of the brain.

In addition, the system may provide for overlays of veins, viable grey matter, and arteries, presented relative to an approach. From this information, the impact of an approach can be better assessed. For instance, the system may calculate the total volume, or number, or length of fiber tracts that may intersect the port at a given point, or along a given trajectory. This can be expressed by the system and method as a total number (such as a histogram for example) may be weighted in order to express a pre-defined, or a user input hierarchy for nerve bundles and fascicles. In some embodiments this calculation can also be made by the system and method with respect to blood vessels in the brain, or with respect to major fiber bundles, or banks of tissue that are critical such as the motor strip. The distance and the angle that a surgical device, such as a port makes to the bank can, in some embodiments, be calculated as an additional metric. Major fiber bundles that the system may apply this processing to may include the corona radiata, or optic chiasm, as some non-limiting examples.

In some embodiments, the system and methods can also use inputs on the general orientation of the fiber relative to the patient frame to weight fiber bundles. For example, the systems and methods may assign different weightings to fibers that can be calculated in the sum total of the impact of the trajectory. In some embodiments, the hierarchy for fibers could be color weighted, such that fibers assigned the color red would be dominant those assigned the color blue, and fibers assigned the color blue would be dominant to those assigned the color green. In other embodiments, the system and method may use color on the rendering to define fiber orientation relative to the port. For example, fibers that are substantially perpendicular to the port may be colored as red, while fibers that are within the tolerance of damage could may be colored blue, and fibers that are outside the tolerance of damage may be colored green. Alternatively, in some embodiments, a fractional an-isotropy map may be used by the system and method to represent fiber connectivity, such that colors attributed to such a representation could be scaled to correspond to the weighing of fibers.

In some embodiments, the system and methods may select a minimally invasive path which tends to follow a sulcus to the lesion of interest and deforms the sulcus as minimally as possible. In such embodiments, the system and method may determine the total distance from a sulci for a given port trajectory, which may be expressed for example as an integrated distance along the port, or a total amount of deflection required to align a port path to a sulci. When measuring a sulcus approach, the total amount of grey or white matter traversed tends to be a critical metric of the system and method. This may be calculated by the system and method from 3D models, and displayed as measurements in millimeters, or other units, or for example, as a ratio of grey matter, white matter and sulci traversed. In some embodiments, the system and methods may associate different weightings to different types of tissue (for example grey matter, white matter and sulci), as well as the fascicles impacted. This may be calculated from the port position, but in some embodiments may be measured with additional inputs accounting for the displacement of the sulci when the port is inserted, and the sulci follows the outer contours of the port.

In some embodiments, the system and method may process inputs on the basis that the introduction of a surgical access port, and an introducer, for example, will tend to displace a significant amount of tissue internally, as well as displace the folds of sulci as it is pushed into the brain. For tissues that are stiffer than the surrounding brain tissue, for instance some clots/hematomas, cellular tumors, the system and method may account for the expected internal shift of tissue as the introducer pushes against the tissue. This displacement may be predicted or measured for example by the system and method with accurate simulation, using apriori tissue stiffness information, geometric knowledge of an introducer and port, a biomechanical model of tissue deformation, (using the skull as a boundary condition, the port as a boundary condition) and using pre-operative imaging data. In some embodiments, the user may modify numerous variables for modeling, such as relative stiffness of a tumor and surrounding tissue as disclosed in copending PCT Patent Application Serial No. PCT/CA2014/050243 entitled SYSTEM AND METHOD FOR DETECTING TISSUE AND FIBER TRACK DEFORMATION, which is incorporated herein in its entirety by reference.

User or system and method implemented changing these values, allowing for visual outputs relating to how the tumor may move within the brain volume may provide a good sensitivity analysis for an insertion approach to be taken. In some embodiments, the stiffness can be predicted based on T2, diffusion and contrast information, however it can also be measured directly from elastography imaging (ultrasound, MRI or OCT, for example).

In some embodiments the system and method may process inputs and generate outputs based on the concept that the sulcus in contact with a port will deform the surrounding sulci to match the surface of the port. The system and method may model this interface using a biomechanical model wherein the sulcus tissue will be at a sliding boundary interface with the port. As the diffusion fibers, and blood vessels that are attached to the surface of the sulci, typically terminating at the ends near the surface of the brain, and running more parallel lower, will tend to track with the sulci, another boundary condition processed by the system and method may be that the fibers track with the sulci displacement. The network of fibers can then be used as registration points and act as connections as part of a 3D network with their own stress and strain profiles. The global deformations of the brain may be modeled by the system and method using continuity of the sulci, vessels, and major structures.

The system and method may update this process and model using real-time imaging information input(s) as the introducer is positioned inside the patient, for example, the patient's head. In some embodiments the real-time imaging may performed using an in-situ port. For instance, real-time ultrasound imaging performed on the tip of the port, may detect tissue stiffness inside the brain. This information can be used by the system and method instead of the priori-predicted stiffness, and can provide an estimate of tissue movement. In addition, ultrasound may be used to identify sulci patterns as a port is being introduced into a patient. These actual sulci patterns may be matched by the system and method to pre-operative sulcus patterns, and a deformed pre-operative model may be generated based on this information. In this iterative manner, the model will be updated by the system and method according to information obtained during the procedure to provide for accurate representations of the tumor location, for instance modeling of tumor roll within the brain, and also the ability to measure the total stress and strain on nerve fibers as the port is inserted into the brain. This may be represented by the system and method as a global value and as with the weighting of the hierarchy of the fibers, the actual strain of the fibers may be used to calculate a value associated with the invasiveness of a surgical approach.

In some embodiments, the system and method disclosed herein may be used to better model the proposed movement of a surgical device, such as a port within a patient's body, such as their tissue, to allow for removal of a tumor that is larger than the opening at the end of the port. In this embodiment, sweeping of the port to access all boundaries of the tumor may modeled by the system and method based on the fixing of the port at the surface of the brain. For example, when the port is moved through different locations of the tumor, the movement of the port may displace the fibers, and the biomechanical model can be used to measure the stress and stain profile across the fibers in the brain as discussed previously. In some embodiments, the system and method may include additional strain gauges located on the outside of the port to measure these effects in-real-time. These values may correlate with the planning model of the brain, and indicate to the surgeon when they are disconcordant or when a tolerance threshold that is pre-determined has been exceeded.

Additionally, as the port is moved, tissue may be removed in volume indicated by the surgeon. The biomechanical modeling components of the current system and method would then calculate the new tissue position through the local volume. Additional real-time imaging may be performed by the system to validate the new tissue boundaries. For example, if real-time imaging with navigational positioning information is available, such images can be compared with the estimated position of the calculated tissue. Such comparison can be done directly if similar contrast is used in both cases, or in a mutual-information sense if the data is not directly comparable. The system can then report the quality of agreement between the new data and the estimated tissue positions. Further still, in some embodiments, the system and method may include robotic or semi-robotic manipulators for use in a similar context. The input to the robot may be strain gauge metrics measured directly in-vivo, and/or using in synchrony with stresses and strains predicted in the surgical planning model. The ability of the system and method to measure fine stresses and strains may be useful in surgical intervention involving other brain injuries and diseases such as TBI (traumatic brain injury), Parkinson's, Multiple Sclerosis (MS), and Alzheimer's disease.

In embodiments, there is a system comprising of a computer or processing system, pre-operative images from various modalities (MRI, CT, PET, etc.), a tracking or navigation system (optional in case of planning system), a single or set of input devices (keyboard, touch screen, mouse, gesture control, etc.), a single or set of output devices (a monitor, a laser pointer, etc.), pointers or tools that act as pointing devices, (optional in case of planning system), tracked surgical devices, such as, scissors, ablation devices, suction cutters, bi-polars, (optional in case of planning system), tracked access port devices and guidance guided (such as automated, semi-automated or manually positioned with alignment feedback) external imaging system (to facilitate delivery of external imaging modalities, aligned to deliver imaging through the access port devices). The system can be used as a surgical planning system, i.e. wherein intra-operative guidance and intra-operative imaging is not part of the system; or as a combined planning and intra-operative guidance system where information collected during the surgical procedure is used to guide next surgical steps, or measure predicted patient outcome.

In some embodiments, the present system may include surgical simulation components, for example robotic systems with haptic feedback. In some embodiments, the simulation features provided by the system and methods disclosed herein can also incorporate a phantom that can be used for training and planning of a specific surgical procedure, as well as imaging of the phantom. An example of how to make a brain phantom for both imaging and biomechanical training of the brain of the patient being operated on is disclosed in International PCT Patent Publication No. WO2015/003271 which is based on International PCT Patent Application No. PCT/CA2014/050659 which corresponds to U.S. Provisional Patent Application Ser. No. 61/900,122 and Ser. No. 61/845,256, respectively, which are incorporated herein by reference in their entirety.

Features of this phantom may include: texture closely mapping the human brain such that insertion of the surgical port along the sulci can be practiced; anatomically correct brain structure to closely emulate the specific patient's brain which can be established by methods such as MRI well in advance of a surgery; emulation of the presence of a tumor of the right type and at the right location in the phantom (for example, the tumor can be identified a priori as soft and free flowing or highly cellular and dense. This information may be incorporated in the creation of the simulated brain to closely match the placement of a tumor to the information inferred from pre-op imaging modalities and to allow the surgical team to evaluate the specific surgical procedure and approach in the context of the specific patient); emulation of the presence of blood vessels with for example, colored fluid to emulate vein structure immediately below the scalp; and emulation of the presence of skull and dura through, for example, the use of a mouldable rigid material such as cast material. The durum may be emulated through the use of polymer sheets that are thin and have substantial durometer such that the synthetic dura displaces during the surgical opening step. The presence of synthetic skull may enable the surgical team to practice opening of a cranial port during a simulation of the craniotomy.

Persons of skill will appreciate that in all methods where a quantitative approach is used to calculate trajectories for port positions, an algorithm may be used to calculate a ranked set of trajectory paths that a user can select from. The user, such as a surgeon, may search these options based on differing criteria such as minimizing global fascicle involvement, minimizing vessel involvement, or minimizing total nerve fiber strain.

Further, in some embodiments, once a trajectory has been selected, the system and method may search a database of prior cases for similar trajectories used in the context of, similar tumor sizes, locations, and DTI fiber map tracts. The outcomes associated with those approaches may be compared by the system and method, and may be presented so as to impact trajectory selection. In some embodiments, actual intra-operative data could be referenced, for example strain measurements in vivo, or DTI maps post-operation.

In use, the systems and methods of this disclosure may be used for surgical procedures wherein there is a need to spare critical structures that can be imaged using pre-operative or intra-operative imaging modalities. The surgical planning aspects of the present method and system may be useful in minimally invasive access procedures including port based neurosurgical procedures and endo-nasal approaches such as corridor based procedures, endo-nasal procedures, port based procedures (rigid fixed diameter), tumor resection, stroke tissue resection and reperfusion, ICH vessel clipping, biopsy via sulci, stem cell recovery, DBS system delivery, catheter based (flexible, smaller diameter). Although the systems and method described herein have used port based surgery, and surgical tools, as examples, the scope of this invention should not be limited by the embodiments set forth in the examples, but should be given the broadest interpretation consistent with the description as a whole.

The systems and methods described herein may be used in applications such as spinal surgical procedures, tumor resection, disk repair, alignment of tendons, pain management, functional device implantation, neck or sinus surgery, functional surgery, cardiac or pulmonary surgery, cardiac function, lung cancer removal, removal of clot or diseased tissue, body cancer or colon imaging, polyp removal, liver, prostate, kidney or pancreas imaging. Persons of skill will appreciate that the methods and systems described herein are not limited to the uses and surgical procedures described above, but can be extended to a variety of procedures that utilize imaging, planning and navigation.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, C# SQL or any other suitable programming language and may comprise modules or classes, as is known to those skilled in object oriented programming. At least some of the elements of the system that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Thus, while some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable storage medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Figure 6:
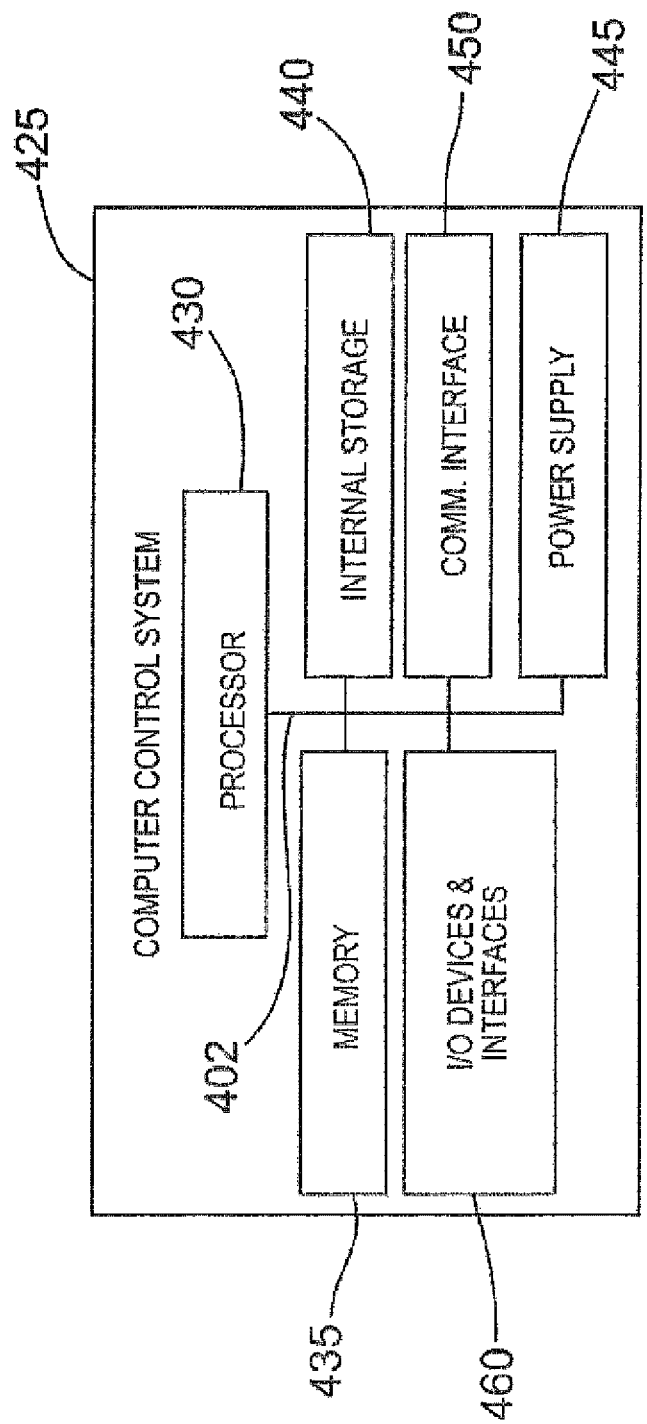
FIG. 6 shows an exemplary, non-limiting implementation of computer control system for implementing the planning and guidance method and system disclosed herein.

FIG. 6 provides an exemplary, non-limiting implementation of computer control system 425, which includes one or more processors 430 (for example, a CPU/microprocessor), bus 402, memory 435, which may include random access memory (RAM) and/or read only memory (ROM), one or more internal storage devices 440 (e.g. a hard disk drive, compact disk drive or internal flash memory), a power supply 445, one more communications interfaces 450, and various input/output devices and/or interfaces 460 such as a user interface for a clinician to provide various inputs, run simulations etc.

Although only one of each component is illustrated in FIG. 6, any number of each component can be included computer control system 425. For example, a computer typically contains a number of different data storage media. Furthermore, although bus 402 is depicted as a single connection between all of the components, it will be appreciated that the bus 402 may represent one or more circuits, devices or communication channels which link two or more of the components. For example, in personal computers, bus 402 often includes or is a motherboard.

In one embodiment, computer control system 425 may be, or include, a general purpose computer or any other hardware equivalents configured for operation in space. Computer control system 425 may also be implemented as one or more physical devices that are coupled to processor 430 through one of more communications channels or interfaces. For example, computer control system 425 can be implemented using application specific integrated circuits (ASIC). Alternatively, computer control system 425 can be implemented as a combination of hardware and software, where the software is loaded into the processor from the memory or over a network connection.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 8:
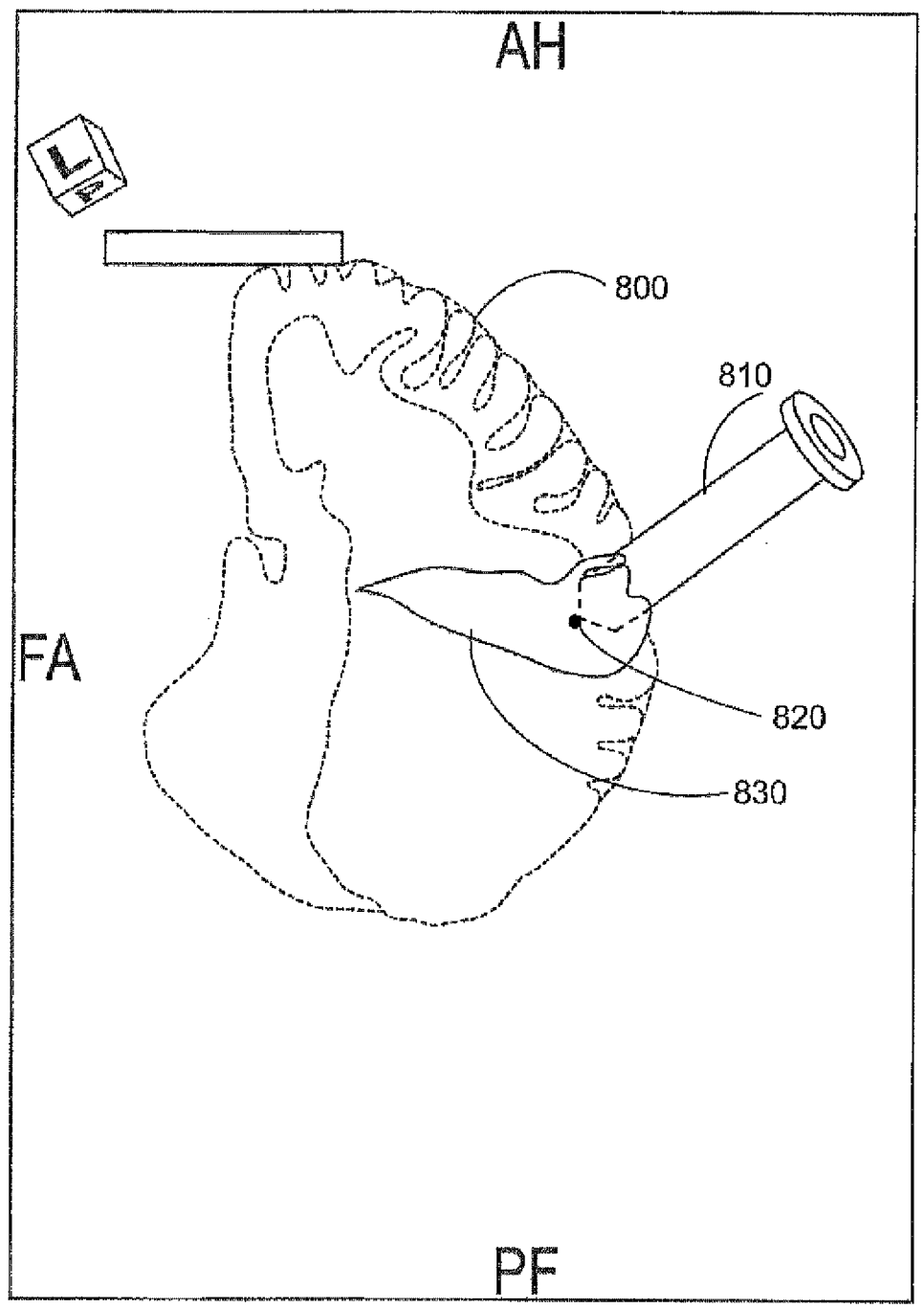
FIG. 8 shows an illustration of highlighting of tracts against 2D patient data expected to be intersected by a surgical tool for a shown pose or orientation.

FIG. 8 depicts one view made available by the surgical planning system. In this exemplary embodiment, the view includes a 2D slice of a brain volume 800, selected by the user, and a virtualized port tool 810 in a specific pose or orientation of the port, where the tip of the port is in contact with a target point 820 within the brain. The target may be the location of a pathology within the brain. The embodiment displays a set of tracts 830, which are anticipated to intersect the tool for this orientation. Tracts are displayed visibly if they intersection the tool on the plane of the current cross-section or within a configurable distance within a range of the cross-section. In the case of port-based neurosurgery, an example of this configurable distance may be 3 mm. The tracts are displayed to the user, and may include red-green-blue colouring (not shown) to indicate the directionality of the tracts in three orthogonal directions. Tracts may be displayed as outlines (i.e., without colour or opacity) if they exist at a configurable distance away from the intersection with the port. Again, for the case of port-based brain surgery, this distance may be typically 3 to 10 mm. This configurable distance may be adjusted to account for the confidence the surgeon may have in positioning his or her surgical tool relative to the intended position when guided by a surgical navigation system. Consequently, this visualization allows the user to perceive DTI tract intersection information in a space around the tool and around the currently visible cross-section (or slice) of the brain 800. When comparing FIG. 8 to FIG. 9, it is evident that the number of tracts shown to the user is fewer in FIG. 8, compared to the number of tracts visible at a different approach angle (or pose) of the same port for the same target point within the brain, in FIG. 9. From this a clinician may infer that the approach of the port tool 810 to the target 820 in FIG. 9 would intersect more tracts than the approach of the tool 810 to the target 820 in FIG. 8.

In an embodiment, a clinician may use a patient-specific imaging volume to aid him or her in choosing an optimal entry point into such patient's anatomy, for example, a sulcus in the brain in order to access a tumor. In a further embodiment, a clinician may rotate the port tool 810 about a target point 820 located within the brain, and employ an embodiment of the disclosed system and method to score alternate approaches, using pre-determined surgical outcome criteria.

In another embodiment, tract information can be used with a mathematical cost minimization process in view of the surgical outcome criteria as disclosed herein to automatically suggest the optimal approaches to a target 620 location within patient anatomy.

Figure 9:
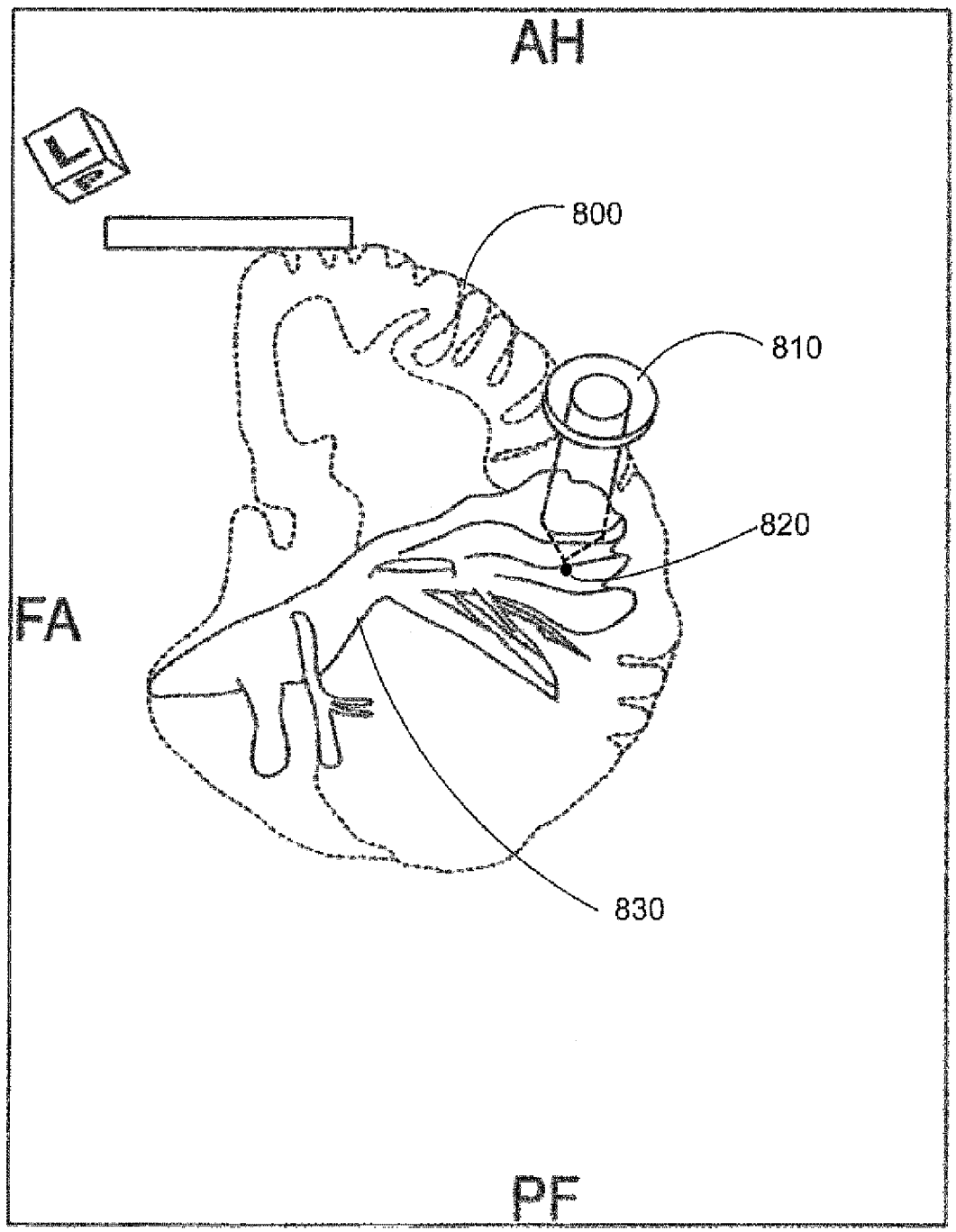
FIG. 9 shows an illustration of the same patient data as shown in FIG. 8, however with different tracts intersected by the surgical tool for a different pose relative to a target in the brain.

FIG. 9 shows an illustration of tracts intersected by the surgical tool for a different pose relative to the pose used to visualize intersected tracts in FIG. 8. In this case, the pose of the tool is depicted as out-of plane to the 2D slice of the patient volume. The tracts are represented using the same rules as described in FIG. 8.

Figure 10:
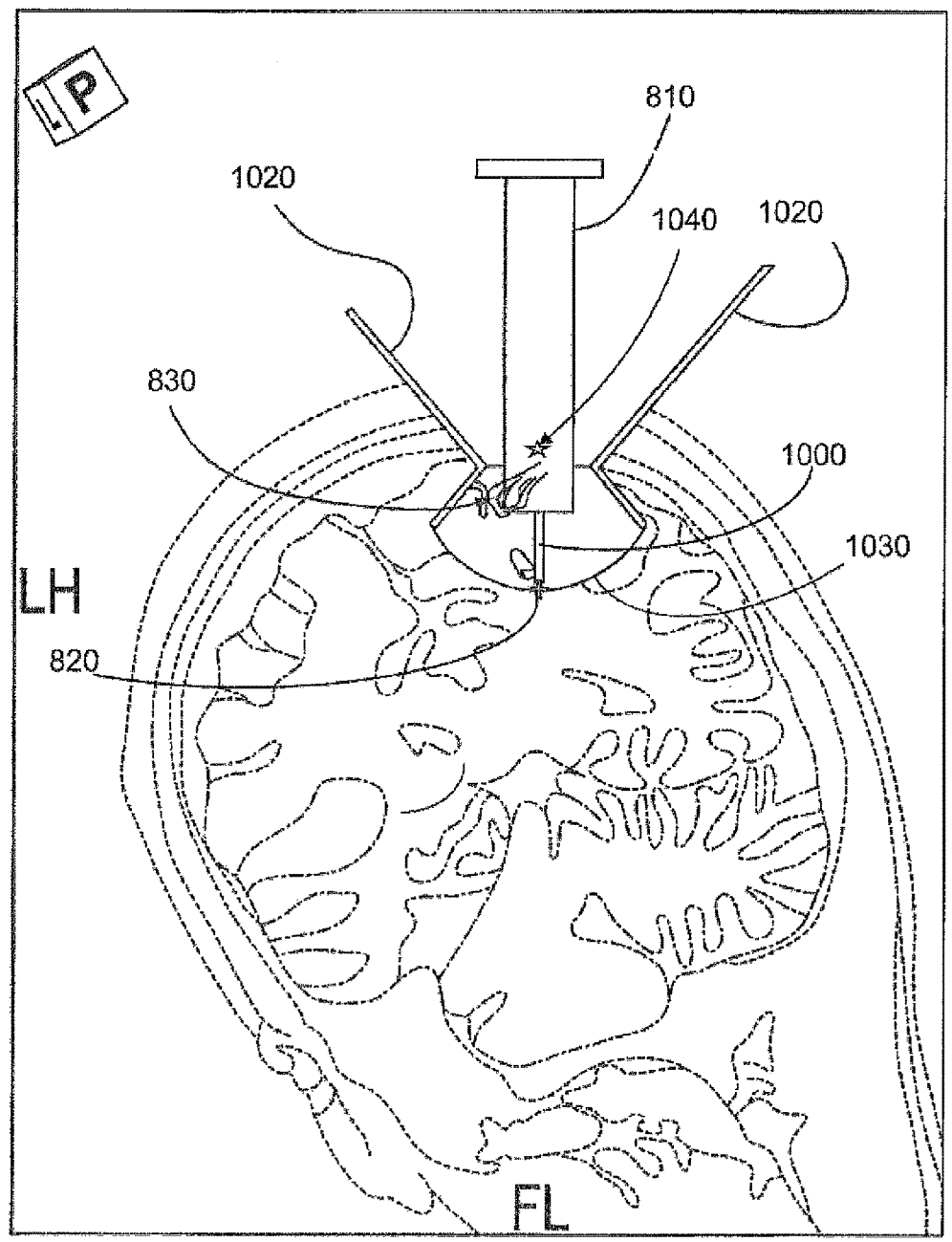
FIG. 10 shows a visualization of craniotomy extent using a selected trajectory and surgical tool, and showing the space available for manipulating the surgical tool during surgery.

FIG. 10 shows a 2D cross-sectional visualization of anticipated craniotomy extent using a selected trajectory 1000 and surgical tool 810. The craniotomy extent is the size of the skull bone that is cut in order to access the brain. In general, the smaller the size of this cut, the less the depressurization of the brain, which will reduce the trauma to the brain. The trajectory 1000 depicts the path along which the tool is inserted. The trajectory may originate at a virtual engagement point 1040 near the surface of the brain and terminate at the target 820. The outward extending lines 1020 illustrate the space available above the scalp for manipulating the surgical tool 810 during surgery. The radial surface extending within the brain region 1030 illustrates the range (or if in 3D, the volume) of brain that will be accessible by the surgical tool for a given size of craniotomy. The surgical tool can be moved in this space to visualize tract intersections 830 and the volume of brain region that will be accessible during surgery. In an embodiment, different sizes of the craniotomy may be selected to evaluate an optimal size of craniotomy, while evaluating the area of the brain that will be accessible by the port tool 810 for resecting the tissue region of interest. This operation may be performed by a human or may be automated using a cost minimization algorithm that incorporates the craniotomy size and volume of accessible region within the brain as the constraints. The minimum volume of accessible region within the brain may be, in one embodiment, the volume of identified tumor in the brain.

Other methods for visualizing patient imaging volumes and overlaying DTI information and displaying virtual surgical tools against 3D renderings of 3D sulcal surface maps, or other 3D imaged patient anatomy, will now occur to a person of skill in the art and are contemplated.

Furthermore, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

While the Applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. A computer implemented method for planning a pathway to a target location in tissue within a patient's body, the computer implemented method executed within a computer system comprising a computer processor connected to a storage medium, and a user interface having a user terminal, the method comprising the steps of:
   producing, at the user terminal, at least one pre-operative image data set image of a 3D volume of a patient's body containing potential entry points into the tissue and one or more targets to be treated;
   receiving through the user interface of the user terminal, inputs to be stored in the storage medium including a list of one or more entry points into the tissue, one or more target locations to be treated, a first target location to be approached first, and a surgical outcome criteria to be satisfied by one or more surgical trajectory paths from the one or more entry points to the first one of the one or more targets;
   computing, at the user terminal, one or more point-wise surgical trajectory paths from the one or more designated entry points to the first target location consistent with the surgical outcome criteria;
   storing the one or more point-wise surgical trajectory paths in the storage medium;
   assigning a score to the one or more trajectory paths, at the user terminal, to quantify how well the one or more trajectory paths satisfy the surgical outcome criteria;
   storing the assigned scores in the storage medium; and
   visually displaying selected surgical trajectory paths at the user interface.

2. The computer implemented method according to claim 1 further comprising the step of
   reformatting the image data set, at the user terminal, to confirm the location of the one or more targets in the 3D volume; and
   storing the reformatted 3D image data in the storage medium.

3. The computer implemented method according to claim 2 further comprising the step of reformatting the image set by visualizing one or more the target locations in at least three orthogonal planes to confirm the location of the one or more target locations in 3D space, at the user interface of the user terminal.

4. The computer implemented method according to claim 1 further comprising the step of computing, at the user terminal, one or more surgical trajectory paths from the one or more entry points to the first target location such that each point-wise surgical trajectory path passes through one or more associated waypoints between the entry point and the first target location.

5. The computer implemented method according to claim 1 further comprising the step of comparing, at the user terminal, the image of the 3D volume to an image of a 3D volume produced from an anatomical atlas and identifies one or more anomalous structures in the one or more target locations.

6. The computer implemented method according to claim 1 wherein the pre-operative image data is a magnetic resonance image of the patient's brain, and wherein the image of the 3D volume is a diffusion tensor image of a volume of the brain containing the one or more target locations to be approached, and further comprising the step of computing
   one or more preferable surgical pathways which do not intercept white matter brain tracks, or,
   one or more preferable surgical pathways which intercept as few white matter brain tracks if not all brain tracks can be avoided, or,
   one or more preferable surgical pathways which intercept selected white matter brain tracks chosen by the clinician.

7. The computer implemented method according to claim 6 further comprising the step of inserting into the 3D image of the brain of the patient, an image of a surgical tool to be used to approach the target.

8. The computer implemented method according to claim 7 wherein said entry points are entry points into the sulci.

9. The computer implemented method according to claim 8 wherein upon insertion of the surgical tool into a particular entry point, the image of the 3D volume of the brain is responsively translated, rotated or both, to allow for visualization of the surgical tool at that particular entry point.

10. The computer implemented method according to claim 9 further comprising the step of assigning different colors, at the user terminal, to brain tissue types of different structure and function in the image of the 3D volume to allow for visualization and identification of a particular type of tissue being intersected by the surgical tool to infer specific functions being impacted due to tissue intersection with the surgical tool.

11. The system according to claim 10 wherein one of the brain tissue types is brain tracks, and the assignment of different colors to functionally different brain tracks are based on a direction they extend in the brain and/or a function they perform.

12. The computer implemented method according to claim 10 further comprising the step of selectively hiding, at the user terminal, portions of the image not in close vicinity to the surgical tool and/or selectively displaying portions of the image in close proximity to the surgical tool.

13. The computer implemented method according to claim 12 further comprising the step of selectively displaying, at the user terminal, white matter brain tracts in an immediate vicinity of each surgical path being computed and hiding white matter brain tracks in all other regions of the 3D image of the brain.

14. The computer implemented method according to claim 13 further comprising the step of selectively displaying, at the user terminal, white matter brain tracks being intercepted by the surgical tool along each surgical path being computed.

15. The computer implemented method according to claim 14 wherein one of said inputs relating to said surgical outcome criteria to be satisfied by one or more surgical trajectory paths from the one or more entry points to the first target includes selecting which white matter brain tracks to intercept and which to avoid intercepting.

16. The computer implemented method according to claim 7 further comprising the steps of calculating at the user terminal, and displaying at the user interface, an amount of tissue distortion upon the tissue being intercepted by the surgical tool during travel along the one or more point-wise surgical trajectory paths from the one or more entry points to the first target location, based on the tissue type and associated mechanical properties of the tissue.

17. The computer implemented method according to claim 7 further comprising the steps of calculating, at the user terminal, and displaying, at the user interface, an amount of distortion and/or rolling of the tumor when approached by, and intercepted by the surgical tool for a plurality of trajectories of approach to the tumor.

18. The computer implemented method according to claim 17 further comprising the steps of visually displaying a simulation of the surgical tool approaching the tumor along the one or more surgical paths and accessing all portions of the tumor for accomplishing tumor resection, at a user interface, once one or more surgical paths have been computed that satisfy the surgical outcome path.

19. The computer implemented method according to claim 18 further comprising the step of displaying, at the user interface, a 3D image of the patient's brain including a skull layer.

20. The computer implemented method according to claim 19 further comprising the step of manipulating the surgical tool during said simulation such that a distal end of the surgical tool can access and resect all parts of the tumor while at the same time a proximal end of the surgical tool maps out a path on the skull that it must follow in order to determine a minimum amount of skull material to be removed during a craniotomy procedure prior to the surgical tool initiating travel to the tumor.

* * * * *